US008864777B2

(12) United States Patent
Harrison et al.

(10) Patent No.: US 8,864,777 B2
(45) Date of Patent: Oct. 21, 2014

(54) METHODS FOR FACILITATING TISSUE PUNCTURE

(75) Inventors: Robert Harrison, Milton (CA); Laura Man Yee Yu, Markham (CA); Neil Godara, Milton (CA); Jeffery Arnett, Gilbert, AZ (US)

(73) Assignee: Anchor Orthopedics XT Inc., Mississauga, Ontario (CA)

(*) Notice: Subject to any disclaimer, the term of this patent is extended or adjusted under 35 U.S.C. 154(b) by 72 days.

(21) Appl. No.: 13/360,768

(22) Filed: Jan. 29, 2012

(65) Prior Publication Data

US 2012/0197282 A1 Aug. 2, 2012

Related U.S. Application Data

(60) Provisional application No. 61/437,275, filed on Jan. 28, 2011.

(51) Int. Cl.
*A61B 17/04* (2006.01)
*A61B 17/12* (2006.01)

(52) U.S. Cl.
USPC .......................................... 606/144; 606/139

(58) Field of Classification Search
USPC .................. 606/139, 142, 144, 145, 147, 148
See application file for complete search history.

(56) References Cited

U.S. PATENT DOCUMENTS

| 4,107,953 A | 8/1978 | Casillo |
| 4,841,888 A | 6/1989 | Mills et al. |
| 5,336,229 A | 8/1994 | Noda |
| 5,342,369 A | 8/1994 | Harryman, II |
| 5,431,666 A | 7/1995 | Sauer et al. |
| 5,462,562 A | 10/1995 | Elkus |
| 5,494,045 A * | 2/1996 | Kiviranta et al. ............. 600/587 |
| 5,507,755 A | 4/1996 | Gresl et al. |
| 5,527,322 A | 6/1996 | Klein et al. |
| 5,591,180 A | 1/1997 | Hinchliffe |
| 5,611,794 A | 3/1997 | Sauer et al. |
| 5,792,152 A | 8/1998 | Klein et al. |
| 5,792,153 A | 8/1998 | Swain et al. |

(Continued)

FOREIGN PATENT DOCUMENTS

| EP | 1354558 B1 | 6/2006 |
| EP | 2011443 A2 | 7/2009 |

(Continued)

OTHER PUBLICATIONS

Arthroscopy Instruments, Arthrex Series I, 2008.

(Continued)

*Primary Examiner* — Dianne Dornbusch
(74) *Attorney, Agent, or Firm* — Nir Lifshitz; Glenn Arnold

(57) ABSTRACT

A method is disclosed for facilitating tissue puncture of a portion of biological tissue using a device, the device comprising a tissue supporting member that is adapted to be placed in a proximal position relative to a portion of the biological tissue and a tissue puncturing member that is adapted to be placed in a distal position relative to the portion of the biological tissue, so that the portion of biological tissue is between the tissue supporting member and tissue puncturing member, the method comprising: supporting the portion of biological tissue using the tissue supporting member; and advancing the tissue puncturing member in a distal direction such that the tissue puncturing member passes through the portion of the biological tissue, thereby puncturing the portion of biological tissue.

17 Claims, 17 Drawing Sheets

(56) References Cited

U.S. PATENT DOCUMENTS

| | | | |
|---|---|---|---|
| 5,797,927 | A | 8/1998 | Yoon |
| 5,814,065 | A | 9/1998 | Diaz |
| 5,836,955 | A | 11/1998 | Buelna et al. |
| 5,843,099 | A * | 12/1998 | Nichols et al. .............. 606/144 |
| 5,935,149 | A | 8/1999 | Ek |
| 5,972,005 | A | 10/1999 | Stalker et al. |
| 6,024,747 | A | 2/2000 | Kontos |
| 6,039,753 | A * | 3/2000 | Meislin .................... 606/213 |
| 6,077,276 | A | 6/2000 | Kontos |
| 6,139,556 | A | 10/2000 | Kontos |
| 6,206,893 | B1 | 3/2001 | Klein et al. |
| 6,241,667 | B1 | 6/2001 | Vetter et al. |
| 6,368,334 | B1 | 4/2002 | Sauer |
| 6,443,963 | B1 | 9/2002 | Baldwin et al. |
| 6,451,031 | B1 | 9/2002 | Kontos |
| 6,461,366 | B1 | 10/2002 | Seguin |
| 6,511,487 | B1 | 1/2003 | Oren et al. |
| 6,517,533 | B1 | 2/2003 | Swaminathan |
| 6,524,321 | B2 | 2/2003 | Kanesaka |
| 6,530,933 | B1 * | 3/2003 | Yeung et al. ............... 606/151 |
| 6,551,330 | B1 | 4/2003 | Bain et al. |
| 6,770,084 | B1 | 8/2004 | Bain et al. |
| 6,984,237 | B2 | 1/2006 | Hatch et al. |
| 6,991,635 | B2 | 1/2006 | Takamoto et al. |
| 7,056,325 | B1 | 6/2006 | Makower et al. |
| 7,060,079 | B2 | 6/2006 | Wulc et al. |
| 7,063,710 | B2 | 6/2006 | Takamoto et al. |
| 7,175,636 | B2 | 2/2007 | Yamamoto et al. |
| 7,211,093 | B2 | 5/2007 | Sauer et al. |
| 7,220,266 | B2 | 5/2007 | Gambale |
| 7,354,443 | B2 | 4/2008 | Moll et al. |
| 7,390,328 | B2 | 6/2008 | Modesitt |
| 7,399,304 | B2 | 7/2008 | Gambale et al. |
| 7,407,505 | B2 | 8/2008 | Sauer et al. |
| 7,445,626 | B2 | 11/2008 | Songer et al. |
| 7,601,161 | B1 | 10/2009 | Nobles et al. |
| 7,632,313 | B2 | 12/2009 | Bhatnagar et al. |
| 7,731,727 | B2 | 6/2010 | Sauer |
| 7,780,684 | B2 | 8/2010 | Wulc et al. |
| 7,815,654 | B2 | 10/2010 | Chu |
| 8,551,121 | B2 * | 10/2013 | Overes et al. ............... 606/145 |
| 2003/0078600 | A1 * | 4/2003 | O'Quinn et al. ............ 606/144 |
| 2003/0083674 | A1 * | 5/2003 | Gibbens, III ............... 606/144 |
| 2004/0092967 | A1 * | 5/2004 | Sancoff et al. .............. 606/148 |
| 2005/0154402 | A1 * | 7/2005 | Sauer et al. ................ 606/139 |
| 2007/0250118 | A1 * | 10/2007 | Masini ...................... 606/220 |
| 2007/0270885 | A1 | 11/2007 | Weinert et al. |
| 2008/0140091 | A1 * | 6/2008 | DeDeyne et al. ............ 606/144 |
| 2008/0214889 | A1 | 9/2008 | Saadat et al. |
| 2008/0262515 | A1 * | 10/2008 | Makower et al. ............ 606/139 |
| 2008/0287967 | A1 | 11/2008 | Andreas et al. |
| 2009/0005793 | A1 | 1/2009 | Pantages et al. |
| 2009/0012538 | A1 | 1/2009 | Saliman et al. |
| 2009/0018554 | A1 | 1/2009 | Thorne et al. |
| 2009/0138029 | A1 * | 5/2009 | Saliman et al. .............. 606/144 |
| 2009/0222027 | A1 | 9/2009 | Sauer |
| 2010/0016889 | A1 | 1/2010 | Ferree |
| 2010/0106194 | A1 | 4/2010 | Bonutti et al. |
| 2010/0114123 | A1 | 5/2010 | Nason |
| 2010/0130990 | A1 * | 5/2010 | Saliman ...................... 606/145 |
| 2010/0145364 | A1 * | 6/2010 | Keren et al. ................. 606/144 |
| 2010/0152790 | A1 * | 6/2010 | Hestad ...................... 606/86 A |
| 2010/0198235 | A1 | 8/2010 | Pierce et al. |
| 2010/0211082 | A1 | 8/2010 | Sauer |
| 2010/0249809 | A1 * | 9/2010 | Singhatat et al. ............ 606/145 |
| 2010/0331863 | A2 * | 12/2010 | Saliman et al. .............. 606/144 |
| 2011/0004226 | A1 * | 1/2011 | Perez-Cruet et al. ......... 606/145 |
| 2011/0015654 | A1 * | 1/2011 | Tsuang et al. ............... 606/144 |
| 2011/0028998 | A1 * | 2/2011 | Adams et al. ................ 606/145 |
| 2011/0066165 | A1 | 3/2011 | Skinlo et al. |
| 2011/0112555 | A1 * | 5/2011 | Overes et al. ............... 606/145 |
| 2011/0152892 | A1 * | 6/2011 | Saliman et al. .............. 606/145 |
| 2011/0276064 | A1 | 11/2011 | Henrichsen et al. |

FOREIGN PATENT DOCUMENTS

| | | |
|---|---|---|
| WO | WO2007009115 A2 | 1/2007 |
| WO | WO2008045376 A2 | 4/2008 |
| WO | WO2008073880 A1 | 6/2008 |
| WO | WO2009005527 A1 | 1/2009 |
| WO | WO2009149455 A1 | 12/2009 |
| WO | WO2010048420 A1 | 4/2010 |
| WO | WO2010085793 A2 | 7/2010 |
| WO | WO2010105046 A1 | 9/2010 |
| WO | WO2010129312 A2 | 11/2010 |

OTHER PUBLICATIONS

OPUS LabraFix Knotless System, ArthroCare Sports Medicine, 2008.
The Material Difference Options for Rotator Cuff Repair, Labral Repair and Suture Management, Biomet Sports Medicine, 2008.
Shoulder Arthroscopy Smith & Nephew, 2008, pp. 1-1 to 1-46.
LSI Solutions. Total Laparoscopic Hysterectomy [Online Video]. http://www.Isisolutions.com/gynprocedurestlh. Published on Dec. 2009 [Retrieved on Feb. 3, 2014].

* cited by examiner

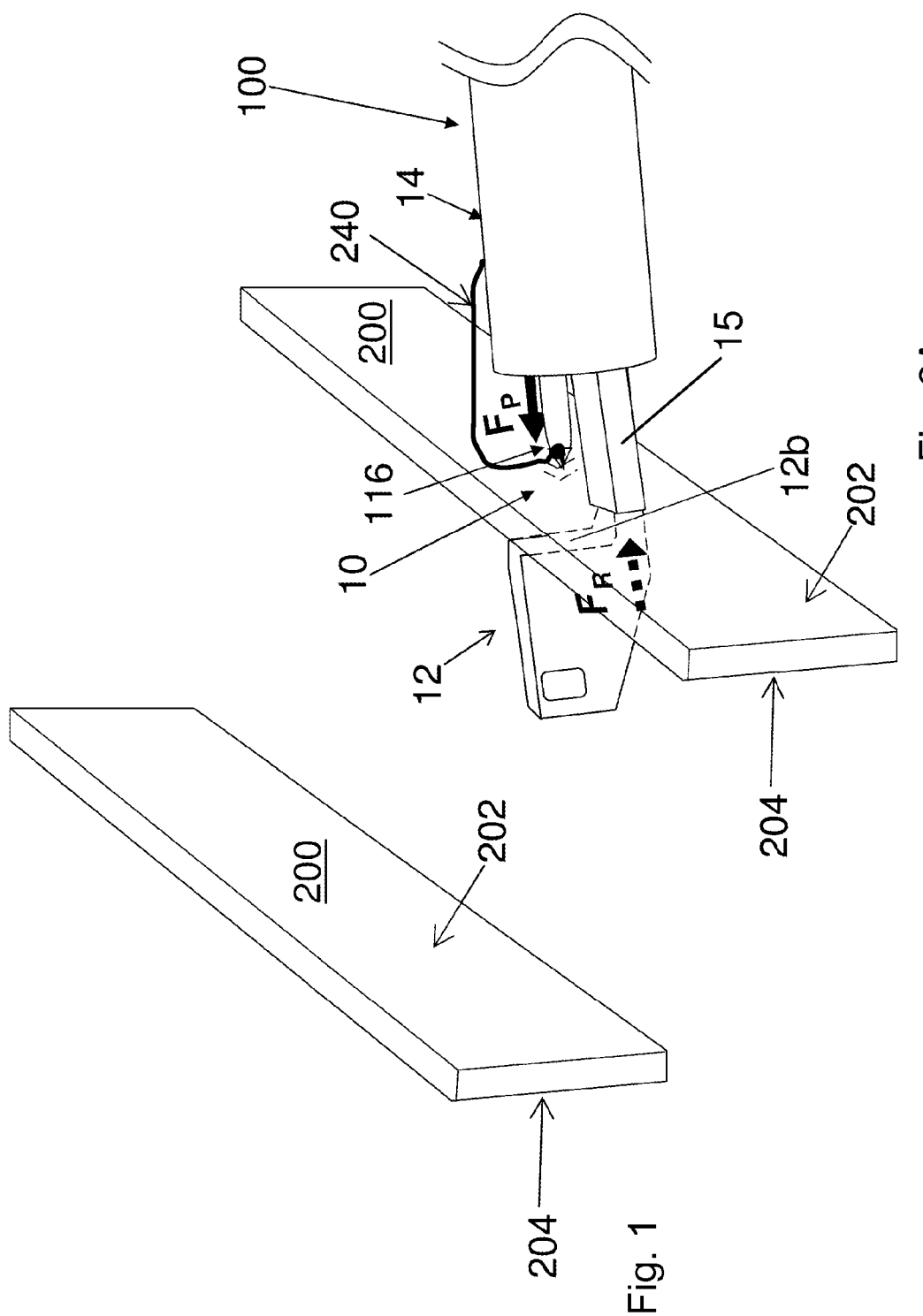

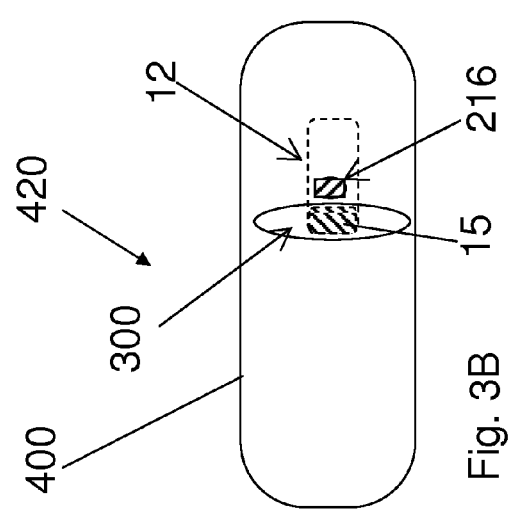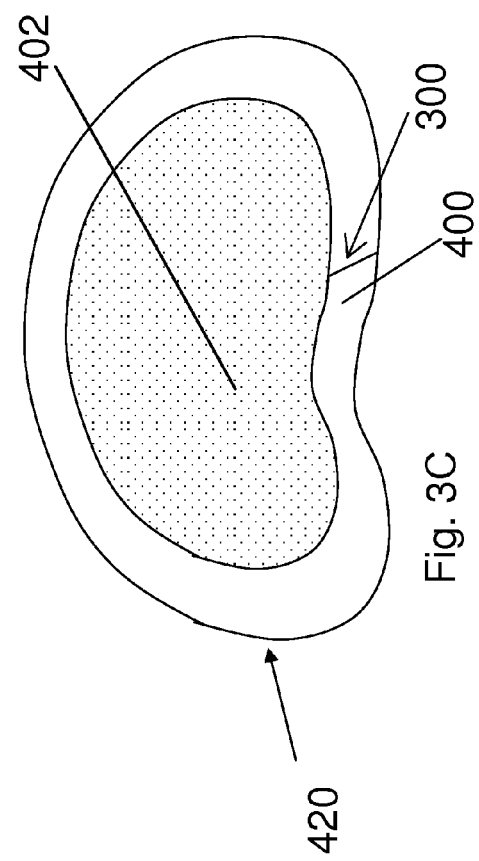

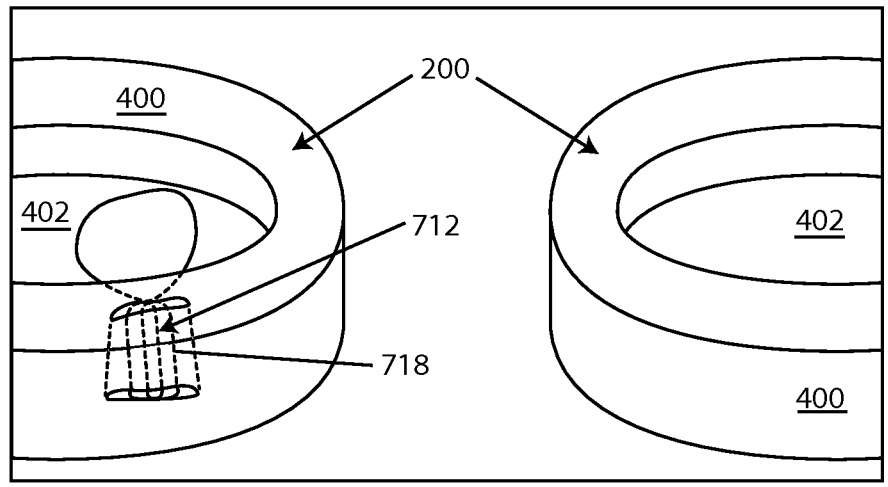
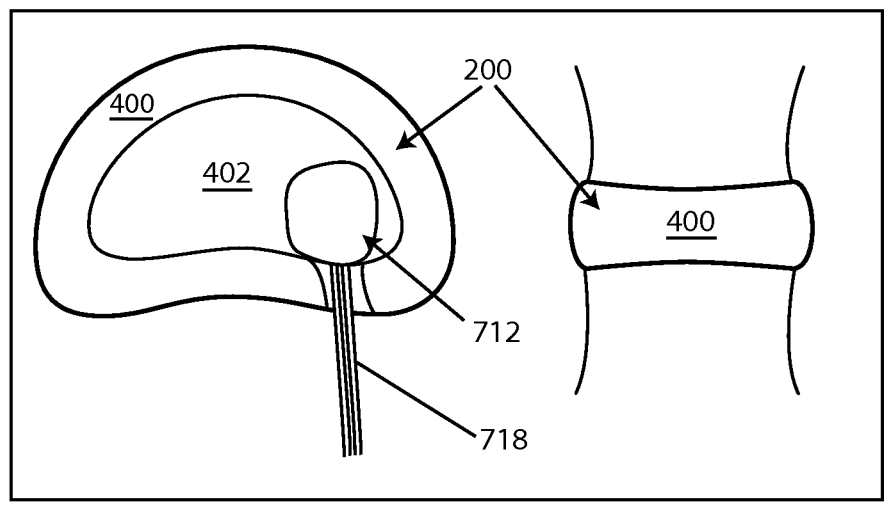
Fig. 10

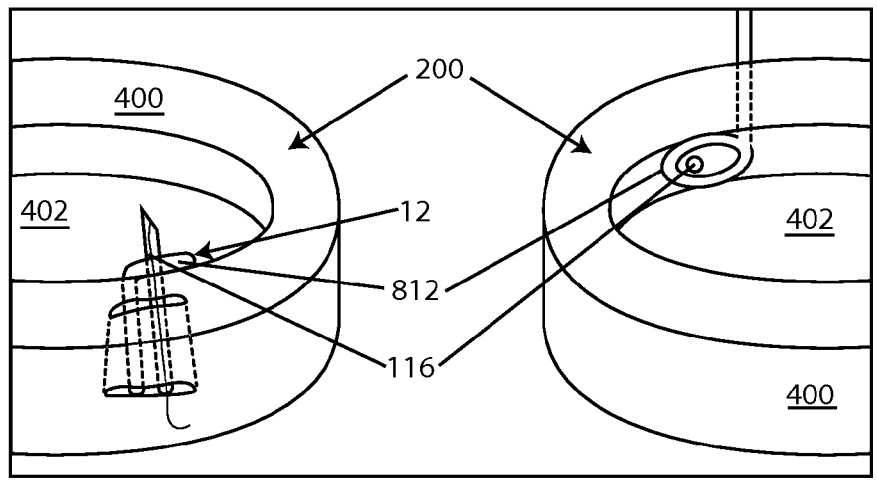
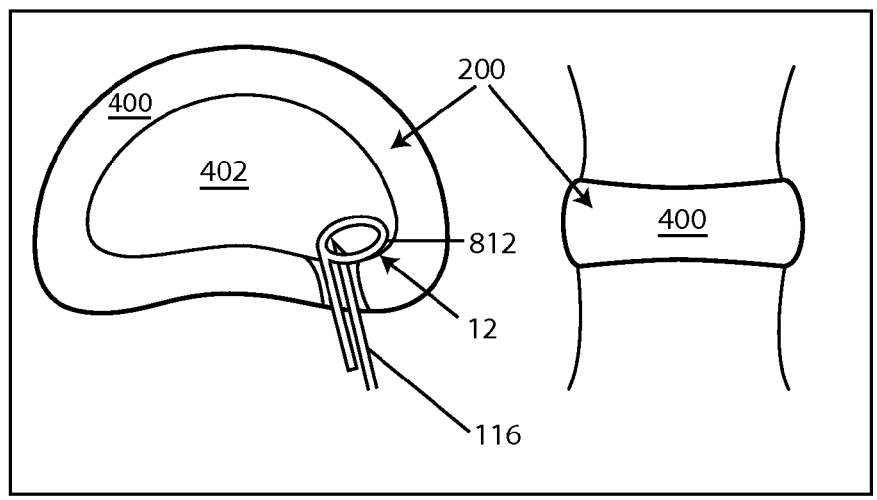
Fig. 11

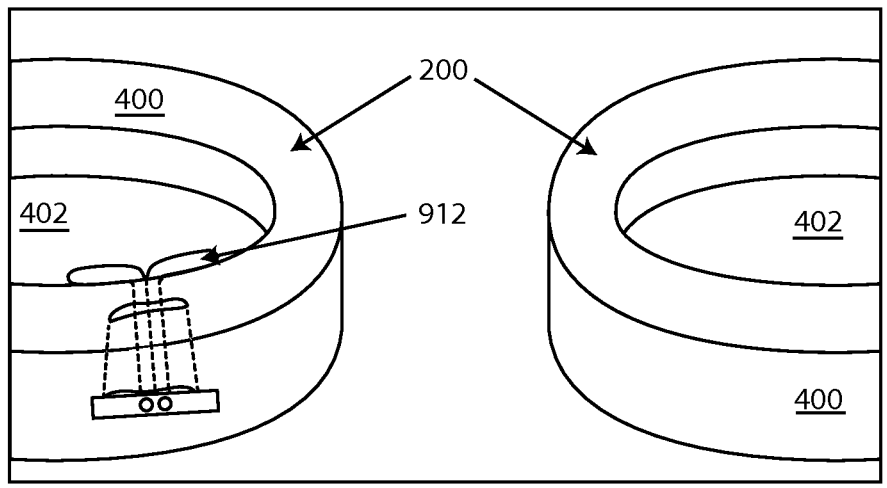
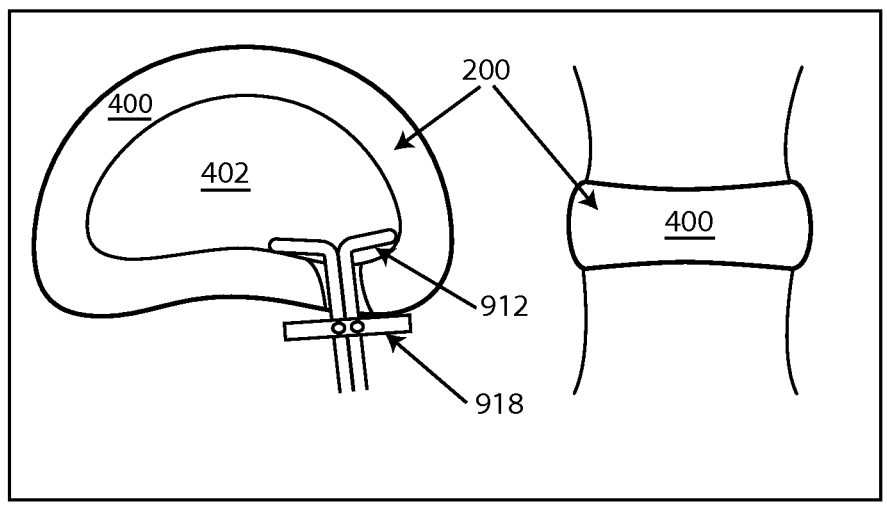
Fig. 12

METHODS FOR FACILITATING TISSUE PUNCTURE

CROSS-REFERENCES TO RELATED APPLICATIONS

This application claims the benefit of U.S. provisional patent application Ser. No. 61/437,275 filed on Jan. 28, 2011, incorporated herein by reference in its entirety.

TECHNICAL FIELD

This invention relates to methods for puncturing tissue, and more particularly, relates to methods for supporting or compressing tissue to facilitate puncturing of the tissue.

SUMMARY OF THE DISCLOSURE

In one broad aspect, embodiments of the present invention comprise a method of facilitating tissue puncture of an intervertebral disc, the tissue comprising a surface to be punctured and an opposing surface, the method comprising: supporting the opposing surface of the tissue opposite a desired puncture site of the surface to be punctured using a tissue supporting member; and puncturing the tissue by applying a longitudinally directed force thereagainst at the desired puncture site using a tissue puncturing member.

As a feature of this broad aspect, the tissue is selected from the group consisting of an annulus fibrosis of an intervertebral disc, a nucleus pulposus of the intervertebral disc and a combination thereof.

In another broad aspect, embodiments of the present invention comprise a method of facilitating tissue puncture of a tissue wall of a body tissue, comprising: supporting a surface of the tissue wall using a tissue supporting member; and puncturing the tissue wall from a substantially unsupported opposite surface using a tissue puncturing member configured for applying a longitudinally directed tissue puncturing force against a region of said opposite surface opposite said tissue supporting member.

As a feature of this broad aspect, the tissue comprises spinal tissue. As an example of this feature, the tissue is selected from the group consisting of an annulus fibrosis of an intervertebral disc, a nucleus pulposus of the intervertebral disc and a combination thereof.

As another feature of this broad aspect, the tissue puncturing member is reciprocally moveable relative to the tissue supporting member for puncturing the tissue wall.

As still another feature of this broad aspect, the steps of supporting a surface of the tissue wall using the tissue supporting member and puncturing the tissue wall using the tissue puncturing member are performed using a single medical device.

As another feature of this broad aspect, the step of supporting the surface of the tissue wall comprises biasing the tissue wall in a direction opposite the tissue puncturing force. As an example of this feature, the puncturing force is less than or equal to a biasing force exerted against the tissue wall.

As still another feature of this broad aspect, the method further comprises the steps of: accessing a defect within the tissue prior the step of puncturing the tissue wall; and delivering a fixation device through the puncture for repairing the defect. As an example of this feature, the fixation device comprises a tissue anchor. As another example of this feature the fixation device comprises a suture.

As another example of this feature, the method is performed using a tissue repair device, the tissue repair device comprises a proximal portion coupled to a distal tip and a tissue receiving gap defined there-between, the distal tip defining the tissue supporting member, and the tissue puncturing member comprises a reciprocally moveable needle held within the proximal portion of the tissue repair device, wherein the step of accessing a defect is performed using the distal tip. In one example, the steps of puncturing the tissue wall and delivering the fixation device are performed substantially simultaneously. In one such specific example, the fixation device comprises a suture coupled to the needle and the step of puncturing involves advancing the needle and the suture coupled thereto, through the tissue wall.

In another broad aspect, embodiments of the present invention comprise a method of facilitating tissue puncture, the tissue comprising a surface to be punctured and an opposing surface, the method comprising: supporting the opposing surface of the tissue opposite a desired puncture site of the surface to be punctured using a tissue supporting member; and assessing a stiffness of the tissue using the tissue supporting member, to determine whether or not the tissue can be punctured using a tissue puncturing member.

As a feature of this broad aspect, the method further comprises: upon determining that the tissue may be successfully punctured, puncturing the tissue by applying force thereagainst at the desired puncture site using a tissue puncturing member. As an example of this feature, the step of assessing the stiffness of the tissue is performed using a pressure transducer.

In another broad aspect, embodiments of the present invention comprise a method of facilitating tissue puncture of a portion of biological tissue using a device, the device comprising a tissue supporting member that is adapted to be placed in a proximal position relative to a portion of the biological tissue and a tissue puncturing member that is adapted to be placed in a distal position relative to the portion of the biological tissue, so that the portion of biological tissue is between the tissue supporting member and tissue puncturing member, the method comprising: supporting the portion of biological tissue using the tissue supporting member; and advancing the tissue puncturing member in a distal direction such that the tissue puncturing member passes through the portion of the biological tissue, thereby puncturing the portion of biological tissue.

In still another broad aspect, embodiments of the present invention comprise a method of facilitating tissue puncture, the tissue comprising a defect, the defect defining an edge region of tissue surrounding the defect, the method comprising the steps of: applying a force to the edge region of the defect to laterally compress the edge region; and puncturing the edge region of the defect.

As a feature of this broad aspect, the method is performed using a tissue repair device, wherein the tissue repair device comprises a proximal portion coupled to a distal tip via a longitudinally extending neck portion defining a tissue receiving gap there-between, wherein the step of applying a force to the edge region of the defect is performed using the neck portion. As an example of this feature, the method further comprises a step of sliding the neck portion through a damaged portion of the edge region prior to compressing the edge region.

As another feature of this broad aspect, the step of applying a force to the edge region to compress the edge region is performed using a retractor.

BRIEF DESCRIPTION OF THE DRAWINGS

In order that the invention may be readily understood, embodiments of the invention are illustrated by way of examples in the accompanying drawings, in which:

FIG. 1 is an illustration of a tissue to be punctured in accordance with an embodiment of a method of the present invention;

FIGS. 2A-2C are illustrations of a device and portions thereof for use in accordance with an embodiment of a method of the present invention;

FIG. 3B is a cross-sectional view taken along the line 3B-3B of FIG. 3A;

FIG. 3C is an illustration of a top view of an intervertebral disc;

FIG. 10 is an illustration of an alternate embodiment of a tissue supporting member in accordance with a method of the present invention;

FIG. 11 is an illustration of an alternate embodiment of a tissue supporting member in accordance with a method of the present invention;

FIG. 12 is an illustration of an alternate embodiment of a tissue supporting member in accordance with a method of the present invention;

DETAILED DESCRIPTION

Figure 2B:
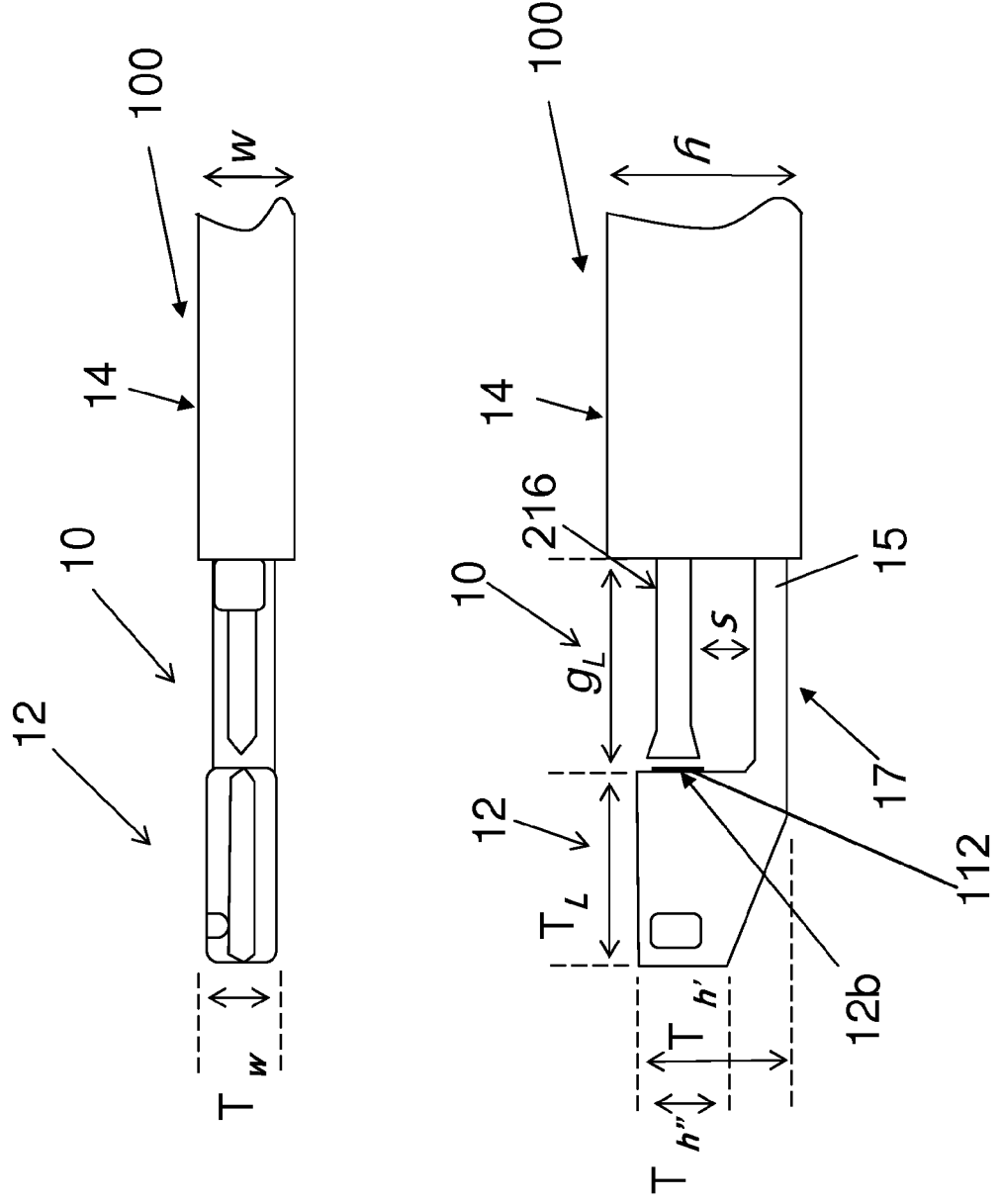

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In accordance with an embodiment of the present invention, a method is disclosed for puncturing tissue within a patient's body, such as soft or floppy tissue. Typically, an opposing tissue surface which is opposite a desired puncture site is supported, and the tissue is punctured by applying a longitudinally directed force at the desired puncture site of the tissue surface to be punctured. The opposing surface is one of an internal tissue surface and an external tissue surface, and the surface to be punctured is the other one of the internal tissue surface and the external tissue surface.

In accordance with one embodiment of a method of puncturing tissue, a desired puncture site is at a proximal face or surface 202 of the tissue 200 shown in FIG. 1. The opposing distal surface 204 of the tissue is supported to stabilize the tissue 200 to enable puncture. The tissue 200 comprises a first surface to be punctured which defines the tissue surface where the puncture is initiated and a second opposing surface. In one example, the first surface is an external tissue surface and the second opposing surface is an internal tissue surface. Whereas, in another example, the first surface is an internal tissue surface and the second opposing surface is an external tissue surface. An external tissue surface refers to a surface that is on the exterior or outside face of an internal body cavity, internal organ, or a region of tissue. An internal tissue surface is used to refer to a surface that is on the interior or inside face of an internal body cavity, internal organ or a region of tissue. The tissue may be supported manually or by using a medical device. In one example, the tissue is supported by using a tissue supporting member and the tissue is punctured using a tissue puncturing member. In some embodiments, a method is additionally provided to assess or test the tissue using the tissue supporting member, by assessing the ability of the tissue to withstand a force exerted thereagainst, prior to puncturing the tissue.

In some embodiments, the puncture is initiated at a desired target location of the tissue surface to be punctured by applying force to the tissue at that location using the tissue puncturing member. Thus, the puncture is first initiated at the tissue surface to be punctured and as the puncturing member is advanced through the tissue, it exits from the opposing tissue surface ensuring that the entire tissue is punctured. As the tissue puncturing member is advanced through the tissue (with the opposing surface being supported by the tissue supporting member), both the surface to be punctured and the opposing surface are punctured. In such embodiments, the puncture is created through the entire thickness of the tissue being punctured (i.e. the tissue puncturing member completely punctures through the tissue including both the surface to be punctured and the opposing surface). In other embodiments, the puncture may be created substantially only through the surface to be punctured and a portion of the tissue thickness (i.e. the tissue puncturing member does not travel all the way through the tissue).

Put differently, in some embodiments, a tissue substrate portion is punctured by a tissue puncturing member, where the tissue puncturing member is moveable between a first position on one side of the substrate portion and a second position where it passes through the substrate portion towards a tissue supporting member on a through side of the substrate portion. In other words, the tissue puncturing member is passed through the tissue from a first side of the tissue to a second side of the tissue. In some embodiments, the tissue puncturing member and the tissue supporting member are separate devices. In other embodiments, the tissue supporting member and the tissue puncturing member are a part of (or components of) the same medical device.

In some embodiments, the tissue supporting member is adapted to be held in a distal position relative to a portion of biological tissue adjacent the portion of the biological tissue to support the tissue, while the tissue puncturing member is adapted to be held in a proximal position relative to a portion of biological tissue, so that the portion of biological tissue is between the tissue supporting member and tissue puncturing member. The distal direction is defined as the direction along the longitudinal axis of the device away from the user, and the proximal direction is defined as the direction along the longitudinal axis of the device towards the user. A force is applied to the tissue puncturing member by extending the tissue puncturing member in a distal direction. The tissue puncturing member is advanced or moved longitudinally in a first, or distal, direction along a path substantially parallel to the longitudinal axis such that the needle passes through the portion of biological tissue, thereby puncturing the portion of biological tissue.

In one specific example, a method is provided of suturing tissue using a device of the present invention as described herein, wherein the tissue puncturing member is a needle attached to a suture, whereby the needle forms a suture incision through which the suture passes. In some embodiments, the tissue puncturing member is retractable longitudinally in a second or proximal direction, after the portion of biological tissue has been punctured. In other words, the tissue puncturing member is adapted to be advanced and retracted substantially parallel to the longitudinal axis of the suturing device.

In some embodiments the tissue supporting member may be inserted through a tissue opening or defect defining an edge region. The tissue supporting member may then be positioned adjacent a distal surface of the edge region of the tissue opening to support said edge region, to allow a tissue puncturing member to be advanced/guided through said edge region to create a puncture therethrough.

Example 1

In some embodiments of a method of the present invention, a medical device 100 is used in order to facilitate puncture within a region of tissue, as mentioned previously. In one specific example, the device 100, as shown in FIGS. 2A and 2B, comprises a proximal portion 14 and a tissue supporting member that is longitudinally spaced apart from the proximal portion 14, defining a tissue-receiving gap 10 therebetween. In one embodiment, the tissue supporting member comprises a distal tip 12 that is coupled to the proximal portion 14 via a longitudinally extending neck portion 15. In other words, the device distal end includes a tissue supporting member including a distal tip 12 and a neck portion 15. The neck portion 15 is coupled to the device proximal portion 14. In some such embodiments, the neck portion 15 connects the distal tip 12 and the device proximal portion 14 along the base 17 of the device. In some embodiments, the neck portion 15 is, for example, substantially rectangular in its cross-section. In other embodiments, the neck portion 15 may be flexible or curved which may aid or enhance device insertion into the tissue or into a defect within the tissue. In one specific example, the neck portion 15 comprises stainless steel and the flexibility of the stainless steel can be altered and controlled through laser patterning to suit a desired application within the tissue.

In accordance with a method of puncturing the tissue using the device 100 as shown in FIG. 2A, the device 100 is positioned such that tissue 200 is received within the tissue receiving gap 10. The distal tip 12 is positioned behind and adjacent to a tissue surface which comprises one of an inner and outer tissue surface (such as the distal tissue surface 204, which thus comprises the opposing surface of the tissue to be punctured). The tissue surface to be punctured, i.e. the proximal surface 202, would be understood to comprise the other of the inner and outer tissue 'surfaces' relative to the opposing surface 204. The distal tip 12 acts as a support structure to support or stabilize the tissue. The distal tip 12 has a tissue engaging surface 12b which can be placed in contact with the opposing surface of the tissue surface to be punctured. In other words, the tissue engaging surface 12b of distal tip 12 is positioned at the distal tissue surface 204 such that it supports the tissue 200. The tissue supporting member allows or facilitates the tissue puncturing member to more readily create a puncture at a desired target location.

In some embodiments, a lack of support of the distal tissue surface 204 (also referred to herein as the opposing surface) may result in one or more of the following: an inability to partially or completely puncture or penetrate the tissue, inaccuracy in puncturing the tissue (i.e. a deviation or deflection from the desired puncture path), and/or damage to neighboring tissues. In other applications, it may be possible to create a puncture without the use of a tissue supporting member, but the use of a tissue supporting member of the present invention facilitates the puncture at the desired puncture site. In other words, tissue displacement (in the direction of the puncture) or tenting may be minimized to allow a puncture to be more readily created at a desired target location.

Once the tissue has been supported using the tissue supporting member, a tissue puncturing member is advanced through the tissue 200 under application of puncture force $F_P$ against the proximal surface 202 of the tissue 200, as follows. The tissue puncturing member is advanced against the tissue surface to be punctured. The tissue contacting or engaging surface 12b helps provide a support force or counter/resistive force $F_R$ against the distal surface 204 of the tissue 200 in the proximal direction. The tissue supporting member resists the displacement of tissue due to application of puncturing force $F_P$ by the tissue puncturing member, thereby providing a resistive force $F_R$ (for example, a reactive force) which allows for or facilitates the tissue puncturing member to puncture the tissue 200. In one embodiment, the puncture force $F_P$ is less than or equal to the resistive force $F_R$. In other words, the puncture force $F_P$ may be viewed as a threshold. If this threshold is less than or equal to the resistive force $F_R$, the tissue may be punctured. In such applications, the tissue supporting member stabilizes the tissue 200 to facilitate puncture.

In some embodiments, the resistive force $F_R$ may be an active force, which may be applied by advancing or retracting the tissue supporting member towards the tissue puncturing member. In some embodiments, the tissue contacting surface 12b of the distal tip 12 has a surface area (SA) which is greater than the SA of a tissue contacting surface of the needle tip or point (which contacts and punctures the tissue). In other words, the cross sectional area of the tissue puncturing member such as needle 116 at its tip or point is less than the cross sectional area of the device distal tip 12 at the tissue engaging surface 12b. Therefore, at the needle point, the pressure exerted on the tissue 200 is much greater than the pressure applied by the opposing tissue supporting member (distal tip 12), thereby allowing the needle to advance through the tissue.

As described herein above, the surfaces of the tissue being punctured may be referred to as a proximal surface and a distal surface defining a region of tissue disposed therebetween, which may be referred to as an intermediate tissue region. Using this terminology, a tissue puncturing member applies a force against one of the proximal and distal surfaces and to the tissue as it translates through the tissue, while a tissue supporting member prevents displacement of the proximal surface, distal surface, and/or tissue as the tissue puncturing member is advanced.

In some embodiments, the supporting force can be applied anywhere on the opposing surface such that the desired entry site of the tissue puncturing member on the tissue puncture surface, along with its desired trajectory, are maintained. In one example, where the tissue puncturing member comprises a needle with a trajectory puncture path, the force against the opposing surface can be applied non-concentrically about the needle trajectory path.

The tissue puncturing member may be a needle 116, having a suture 240 coupled thereto. The distal tip 12 supports the tissue while the needle 116 is moved longitudinally in a first direction along a path substantially parallel to the longitudinal axis such that the needle 116 and the suture 240 pass through the portion of biological tissue thereby puncturing the portion of biological tissue, whereby a suture incision is formed in the portion of biological tissue through which the suture 240 passes. The advancement of the needle 116 transfers the suture from the needle 116, through the portion of the biological tissue between the needle 116 and the distal tip 12, to the distal tip 12. The needle may then be retracted in the proximal direction away from the distal tip 12.

In some embodiments having a needle as the tissue puncturing member, the needle may comprise a bevel tip. In an alternate example, the needle 116 comprises a trocar tip. The needle 116 may be advanced manually or with the aid of a medical device.

The tissue supporting member, such as device distal tip 12, has sufficient rigidity to allow the distal tip 12 to resist the puncture force $F_P$ and support the tissue. In some examples, as shown in FIGS. 2A and 2B, the tissue supporting member is a part of a curved or c-shaped device distal end which can be inserted behind and adjacent the distal tissue surface 204 to stabilize the tissue.

As shown in FIG. 2B, the device 100 comprises a proximal portion 14 having a height h of about 6 mm to about 12 mm. In an example of this, the device proximal portion has a height h of about 7 mm. In some embodiments, the distal tip 12 is longitudinally spaced apart from the proximal portion 14 and has a tip length $T_L$ of between about 2 mm to about 20 mm and a tip width $T_w$ of between about 2 mm to about 10 mm. In an example of this, the tip length $T_L$ is about 7 mm and the tip width $T_w$ is about 2.5 mm or about 3.5 mm.

In some embodiments, the distal tip 12 has a height that tapers from a proximal height $T_{h'}$ of about 7 mm to a distal height $T_{h''}$ of about 2 mm. In one example, the distal tip 12 has a proximal tip height $T_{h'}$ of about 5 mm and a distal tip height $T_{h''}$ of about 4 mm. The tissue receiving gap 10 has a gap length $g_L$ of between about 2 mm to about 20 mm. In one example, the gap length $g_L$ is about 8 mm. In another example the gap length $g_L$ is about 10 mm. In some embodiments, a needle/shuttle assembly 216 is positioned at a height of between about 1 mm to about 4 mm from the device base 17. In some embodiments, where the needle/shuttle assembly is used to deliver suture to repair a defect through stitching, this may provide a stitch offset S of between about 1 mm to about 4 mm.

Figure 2C:
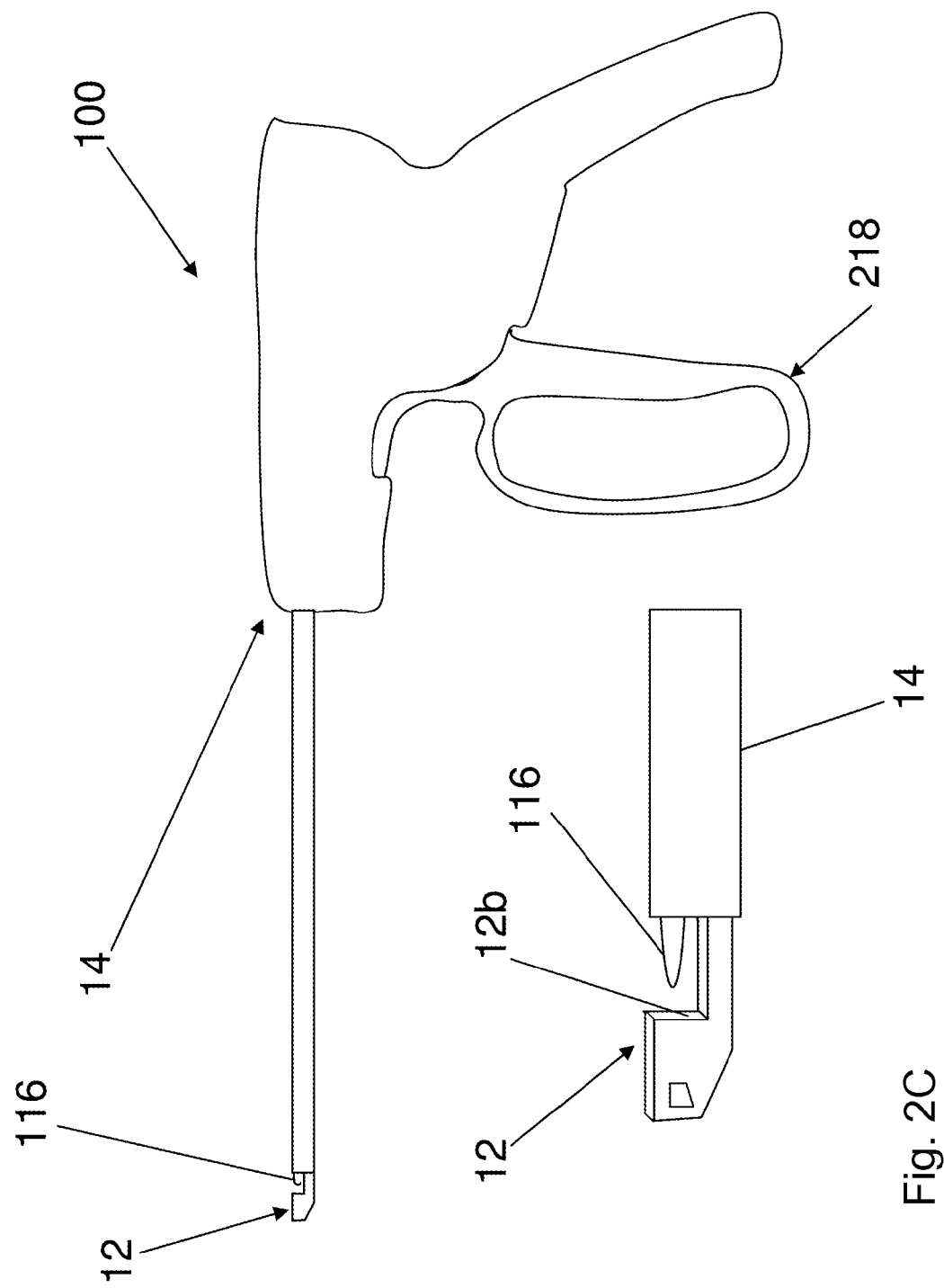

In some embodiments, the puncturing member and the tissue supporting member are a part of the same device 100 as discussed above. In one example, the tissue puncturing member such as the needle 116 is housed within the device proximal portion 14. In some embodiments, the needle 116 is trigger actuated. In other words, the needle 116 is advanced with respect to the proximal portion 14 and the distal tip 12 of device 100 upon actuation of a trigger such as trigger 218 in FIG. 2C. The needle 116 translates longitudinally from the proximal portion 14 of device 100 into the distal tip 12 as it punctures the tissue. In other words the needle 116 can be advanced in a direction along the longitudinal axis of device 100 and it moves for example, from a proximal side of the tissue 200 and through the tissue to the distal side of the tissue 200. In an alternate embodiment, a static needle 116 may be provided and a moving tissue supporting member/surface may be provided that urges the tissue against the needle allowing the needle 116 to puncture the tissue. In one example, the needle 116 is a reciprocating needle which is retracted proximally back towards the proximal portion 14 of the device, for example, upon actuation of a trigger. Thus, for example, the needle 116 moves from the distal side of the tissue 200 to the proximal side of the tissue 200. In one embodiment, additional support is provided on the proximal side of the tissue when the needle 116 is retracted.

In one application of an embodiment of a method as described herein, device 100 is used to puncture spinal tissue. In one example of this, the device 100 is used to puncture tissue of the annulus fibrosis 400 of the intervertebral disc. In other embodiments, the device 100 is used to puncture soft tissues, including but not limited to muscle tissue, blood vessels, abdominal tissue for example, stomach wall/lining, ligaments, tendons and fatty tissue. In still other embodiments, the device 100 may be used to puncture other types of tissue.

Example 2

Figure 3A:
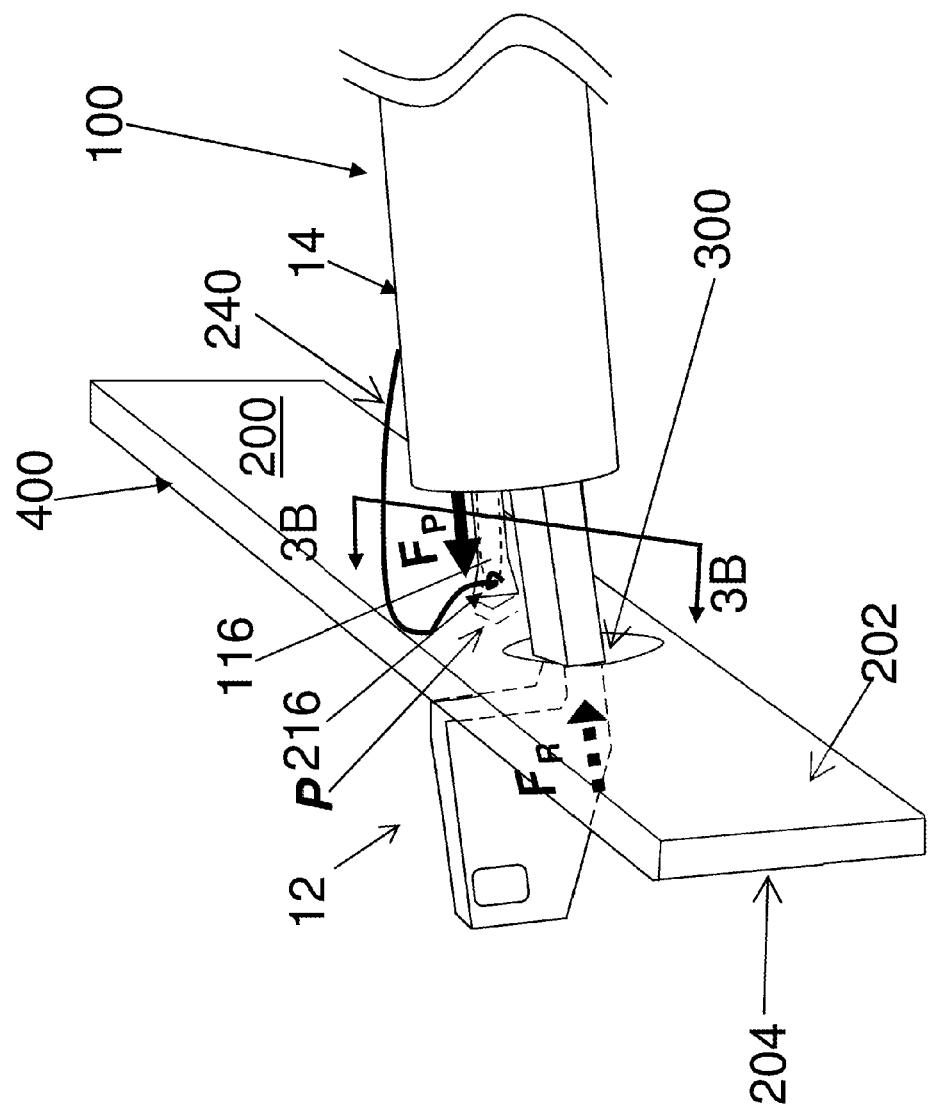
FIG. 3A is an illustration of a method in accordance with an embodiment of the present invention.

In alternative embodiments of the present invention, a method is provided for repairing a defect within a region of tissue within a patient's body. The method comprises a step of accessing a defect prior to puncturing the region of tissue and delivering an article or implement, such as a fixation device, through the puncture in order to repair the defect. The device 100 is inserted at the site of the defect 300, as illustrated in FIG. 3A, to allow a tissue puncturing member to be passed from the proximal side of the tissue 200 (for example, the external surface of the tissue), to the distal side of the region of tissue 200 (for example, the internal surface of the tissue). In one example, the tissue puncturing member is a needle/shuttle assembly 216. In another example, the tissue puncturing member is a needle 116. A tissue supporting member is positioned on the distal side of the tissue adjacent the tissue distal surface 204 and facilitates puncturing of the tissue using the tissue puncturing member. In other words, the tissue supporting member is introduced through the defect 300. A desired puncture site P is defined at some distance from the defect 300. In one example, some of the tissue disposed between the defect 300 and the desired puncture site P is of poor quality and the use of the tissue supporting member maintains the desired trajectory of the tissue puncturing member (such as needle 116) which would otherwise be altered by undesired tissue displacement.

In one example of this method, the tissue puncturing member further allows a fixation device to be carried from the proximal side of the tissue to the distal side of the tissue, for example, to repair the defect 300. In some embodiments, the tissue puncturing member itself carries the fixation device from the proximal to distal side of the tissue while puncturing the tissue. In other embodiments, the tissue puncturing member creates a puncture to allow access for the delivery of a fixation device therethrough. In one example, the tissue puncturing member comprises a needle/shuttle assembly 216 and the fixation device for repairing the defect is a suture 240.

Alternatively, a suture may be delivered using a delivery method other than the needle/shuttle assembly 216. In another example, the fixation device for repairing the defect is an anchor.

In one specific example of a method of repairing a defect, a shuttle/needle assembly 216 is used to pass a suture 240. As the needle/shuttle assembly 216 of device 100 is advanced against the tissue, it applies a force against the proximal surface 202 of the tissue in order to puncture the tissue near the defect 300 at the desired puncture site P. In one example, the supporting member, which (as illustrated) is a distal tip 12, is positioned behind or distal to the distal tissue surface 204 and prevents the tissue from buckling or becoming displaced into the defect, which helps the needle/shuttle assembly 216 to more easily puncture or pierce the tissue, and/or helps to ensure that the trajectory of the needle/shuttle assembly 216 through the tissue 200 is substantially similar to the intended trajectory. The tissue supporting member, as shown by distal tip 12, is inserted through the defect 300 and positioned on the distal side of the tissue. The tissue contacting surface 12b of the distal tip is positioned adjacent the tissue distal surface 204. As mentioned above, the tissue supporting member such as distal tip 12 helps stabilize the tissue 200 to allow advancement of the needle/shuttle assembly 216 through the tissue 200 under application of puncture force $F_P$ against the proximal surface 202 of the tissue 200. The supporting member exerts a support force or a counter/resistive force $F_R$ against a distal surface 204 of the tissue 200, the force being directed proximally, which limits or prevents the tissue 200 from displacing distally as the needle is pressed against the tissue 200. This allows or facilitates the needle/shuttle assembly 216 to puncture the tissue 200. In the embodiment shown in FIG. 2C, a trigger 218 is actuated to advance the tissue puncturing member such as the needle/shuttle assembly 216, such that it pierces the tissue 200. This may aid in passing a suture 240 from the proximal side of the tissue 200 to the distal side of the tissue 200.

In one specific example of a device used in accordance with embodiments of a method of the present invention, the distal tip 12 defines a needle receiving chamber. The needle receiving chamber may be tapered distally to limit the distal movement of the needle 116 within the needle receiving chamber. In one example, the device 100 may comprise multiple needles 116 and corresponding needle receiving chambers within device distal tip 12. Similarly, the multiple needles 116 may be provided as multiple needle/shuttle 216 assemblies which may be used to pass a plurality of sutures.

In some embodiments, the providing support to the tissue such as with a tissue supporting member (for example, device distal tip 12), aids in more accurate puncturing of tissue at the desired target location. The tissue supporting member helps prevent the tissue puncturing member from sliding along the tissue as it is advanced. In other words, the tissue supporting member helps prevent tenting and prevents the tissue puncturing member such as needle 116 from translating away from the target puncture site. In the absence of a support for the tissue, the angle/path or trajectory of the needle 116 may be altered due to tissue tenting and thus the ideal puncture path may be lost. Thus, supporting the tissue helps prevents tenting and helps maintain the desired trajectory of the tissue puncturing device.

Example 3

In one embodiment, the method of the present invention is used to treat a defect 300 within an annulus fibrosis 400 of the intervertebral disc 420 as shown in FIGS. 3A, 3B and 3C. In some embodiments, the defect may be present within tissue of the annulus fibrosis 400, whereas in other embodiments the defect may be present within a combination of the tissue of the annulus fibrosis 400 and the nucleus pulposus 402. Thus, in some embodiments, the tissue supporting member may be used to support a plurality of tissues, for example, tissues of both the annulus fibrosis and the nucleus pulposus. In other words, the distal tip 12 is positioned through the defect 300 within the annulus fibrosis 400 such that it is positioned distal to the inner annulus fibrosis 400, and tissue of the annulus is received within the tissue receiving gap 10. Thus, the distal tip 12 is positioned adjacent the inner surface of the annulus 400. Similarly, the tissue puncturing member may be passed through a plurality of tissues, such as through both the annulus fibrosis and the nucleus pulposus. In some embodiments the defect 300 may be similar to the embodiment shown in FIG. 3A. In other embodiments, the defect 300 may be formed as a part of the surgical procedure, whereby an incision is made into the annulus fibrosis such that flaps are created adjacent the incision (such as those created in some instances of anterior lumbar interbody fusion procedures).

During treatment of a defect within the intervertebral disc, a device 100 is inserted to allow a suture to be passed from the proximal side 202 of the annulus tissue 400 to the distal side 204 of the annulus tissue 400. In one example, a needle 116 and/or needle/shuttle assembly 216 is used to pass a suture 240. However, during treatment of this soft tissue defect 300, advancement of the needle/shuttle through the proximal side 202 of the annulus fibrosis 400 without the use of a tissue supporting member may cause the annulus tissue to tent or buckle or otherwise become displaced which may lessen the ability of the needle and/or shuttle to puncture, penetrate or pierce the annulus tissue, or reduce the ability of the needle and/or shuttle to puncture along the intended trajectory. The tissue puncturing device such as the needle/shuttle assembly 216 is then advanced through the exterior annulus fibrosis. As mentioned previously, the needle/shuttle assembly 216 is advanced through the tissue by application of force $F_P$ on the proximal surface 202 of the tissue 200 proximal to the site of tissue stabilization (which in this case is the exterior annulus fibrosis surface). The tissue supporting member such as distal tip 12 provides a counter or reactive force $F_R$ against a site of the distal surface 204 of the tissue 200 (which in this case is the inner annulus fibrosis surface). This allows stabilization of the annulus fibrosis 400 to allow puncturing of the annulus fibrosis 400. A suture is passed from the exterior annulus fibrosis to the inner annulus fibrosis and may be used to repair the defect 300 within the annulus 400 using techniques known in the art.

As mentioned previously, in one example, the tissue is punctured near a defect 300 and the distal tip 12 has sufficient rigidity to prevent tissue from displacement or falling inwards or into the defect 300. In one specific example, the distal tip 12 provides support directly behind the desired puncture site on the opposing side of the desired puncture site. If the support is absent, the tissue may become displaced as the needle is advanced and pressed against the tissue, thereby enlarging the defect 300. This may occur in cases where the tissue is of poor quality, such as that of the annulus fibrosis 400 in some patients.

Example 4

Figure 4:
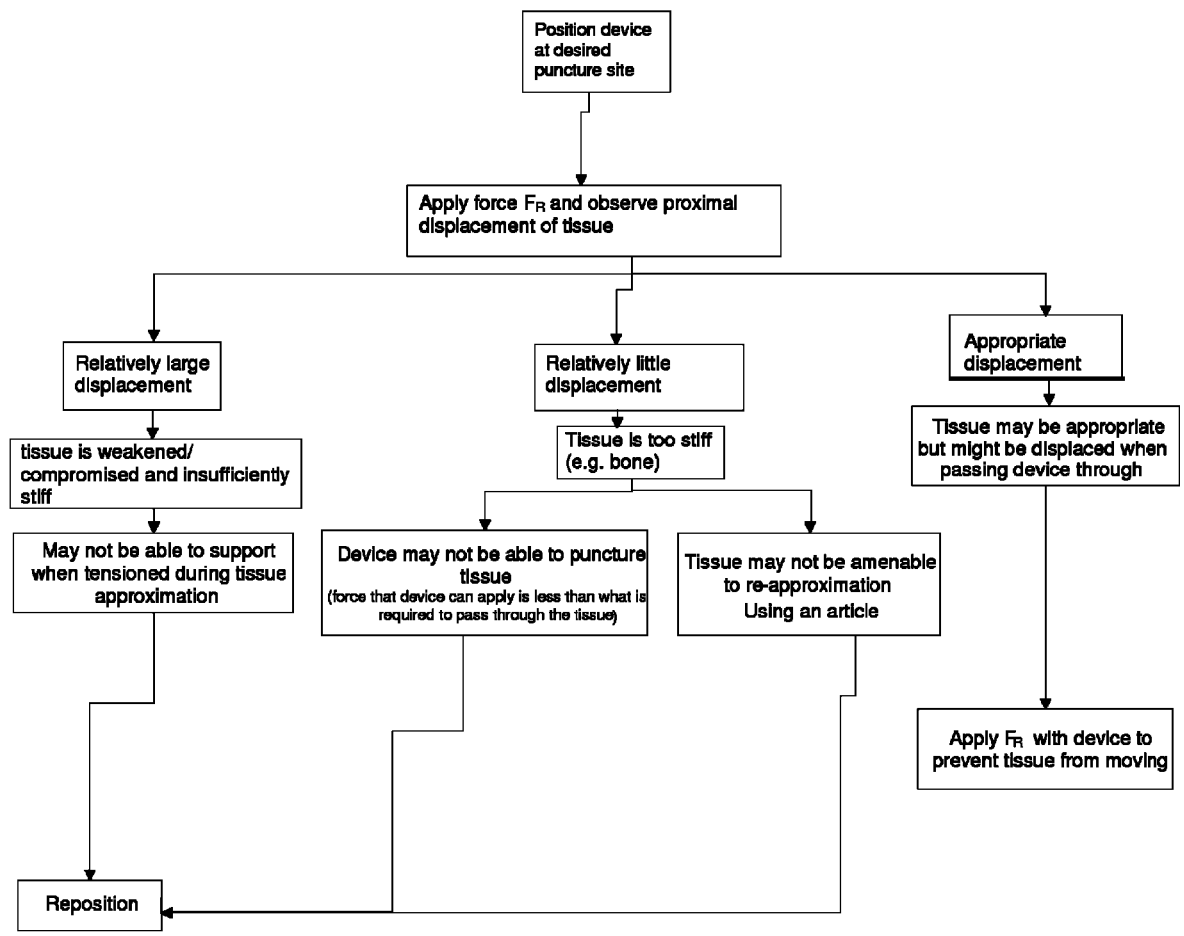
FIG. 4 shows a flow chart illustrating a method in accordance with an embodiment of the present invention.

In some embodiments, prior to puncturing the tissue, the tissue may be assessed using the tissue supporting member, to determine whether the tissue can be successfully punctured using the tissue puncturing member. More particularly, the tissue supporting member may be used to assess the stiffness of the tissue to be punctured. In one specific example, tissue stiffness may be determined by the amount of displacement of the tissue in response to application of a force against the tissue by the tissue supporting member In one particular embodiment as shown in the flow chart provided in FIG. 4, the user (such as a physician) may assess the quality of the tissue prior to puncturing the tissue. Referring to FIG. 4, the device is initially positioned at the desired puncture site. The user may then apply a force $F_R$ against the tissue using the tissue supporting member that has been inserted behind the desired tissue puncture site. Application of a force $F_R$ by the tissue supporting member may provide information regarding the quality or state of the tissue that is desired to be punctured. When force $F_R$ is applied, the proximal displacement of the tissue may be observed in response to the application of force $F_R$. In one specific example, a device 100, as described herein above, is used to implement the method of assessing tissue as presently described. The tissue to be assessed may be positioned within the tissue receiving gap 10. The force $F_R$ may be applied using a tissue supporting member in the form of a distal tip 12 having a tissue engaging surface 12b. In an alternative embodiment, a distal surface of the device proximal portion 14 of the device 100 may be used to assess the stiffness of tissue.

In one application, a force $F_R$ may be applied, for example, against the distal face of a region of tissue adjacent a defect within an intervertebral disc. The tissue supporting member may be inserted through the defect within an annulus fibrosis and positioned such that the tissue engaging surface is placed behind or distal to a region of the annulus fibrosis adjacent the defect. The tissue supporting member may then be pulled back applying force $F_R$ and the deflection of the annulus fibrosis tissue in response to the applied force $F_R$ may be observed. The proximal deflection of the region of the annulus fibrosis provides an indication of its stiffness. For example, the defect may be found in a region of the annulus fibrosis comprising weakened tissue where the matrix of collagen in the layers of tissue forming the annulus is weakened. When the tissue supporting member is pulled back it may slip through the weakened layers of the annulus fibrosis or alternatively a relatively large deflection of the annulus fibrosis may be observed. Under such circumstances, if the tissue was punctured and a suture passed there-through, the tissue may not be able to support the tension applied by the suture as it may not offer substantial resistance to the suture as it is pulled to be approximated. Therefore, relatively large displacement of the tissue may be an indicator of weakened, compromised or insufficiently stiff tissue, which may not be able to provide support when it is tensioned during tissue approximation.

The annulus fibrosis is normally a highly structured tissue having sufficient stiffness to allow a physician to puncture the tissue to pass an implement like a suture there-through. The nominal stiffness of the annulus fibrosis may generally be known to a physician of ordinary skill in the art that is familiar with suturing soft tissues. For example, a physician familiar with annular repair or discectomy, may generally be aware of the differences in relative stiffness of an annulus fibrosis, soft-tissues and bone. Thus if the annulus fibrosis tissue deflects significantly, which may be observed in a relatively large proximal movement of the device, then the annulus fibrosis tissue may be deemed to be insufficiently stiff so as to be able to support suture under tension during approximation of tissue. The device may then be repositioned and the method of assessing tissue may be repeated in order to find a region of annulus fibrosis that is of sufficient stiffness to allow a tissue puncturing member to pass therethrough.

Alternatively, the defect within the intervertebral disc may be located adjacent an end plate of the vertebra. In one such example, the tissue supporting member is inserted through the defect to be positioned adjacent a region of the annulus fibrosis to apply a force $F_R$ thereagainst. When the device is then pulled proximally, if no deflection is observed, this may indicate that the tissue supporting member is likely positioned adjacent a bony surface and is thus positioned adjacent tissue that may be too hard or stiff to allow a needle to pass therethrough. It may additionally indicate that the tissue may not be amenable to re-approximation even it were able to be punctured. Generally, if a relatively small displacement is observed within tissue under application of force $F_R$, it may indicate that the device may not be able to puncture the tissue (in other words, the force that the device can apply is less than what is required to pass through the tissue). For example, a small displacement may indicate that the stiffness of the tissue is too high, such as may be the case with bone tissue. This may further indicate that the tissue may not be amenable to re-approximation using a fixation device such as a suture. The physician may then re-position the device in order to find a region of tissue with suitable stiffness, and may then proceed to puncture the region of tissue using a tissue puncturing member, to pass a fixation device therethrough.

In one example, the fixation device comprises a suture and the tissue may be of suitable stiffness to allow the defect to be approximated using the suture. In other words, once the physician has positioned the device at the desired puncture site and force $F_R$ is applied, displacement of the tissue may indicate that tissue is appropriate or suitably stiff to allow it to be punctured using a tissue puncturing member of the device. However, even when the tissue is found to be suitably stiff, it might be displaced when the tissue puncturing member of the device is passed through it. In one such example, the tissue supporting member of the device may additionally be used to apply a force $F_R$ against the tissue to prevent the tissue from moving as it is being punctured.

The applications provided herein above with respect to assessing properties or qualities of the tissue prior to puncture including soft tissue, normal annulus and bone are but examples (i.e. they are exemplary, but not limiting), and by altering the tissue puncturing member, other tissues of varying stiffness may be regarded as appropriate for puncture (in terms of having suitable stiffness to allow the tissue puncturing member to puncture the tissue).

In one particular example, the tissue puncturing member comprises a needle or trocar that is designed to pass through bone. Similar to embodiments described above, a force $F_R$ is applied against the tissue that is to be punctured and the proximal displacement of the tissue may be observed. However, in this particular example, the tissue may be regarded as being appropriate (or as having suitable stiffness) for puncture when little/minimal displacement of tissue is observed, such as when the device is positioned against bone tissue. On the other hand, and again with respect to this particular example, both the normal annulus and compromised or weakened annulus may be deemed to be insufficiently stiff to support the fixation device to be passed there-through.

In an alternate embodiment, a pressure transducer may be provided on a tissue engaging surface of the tissue supporting member, such as a pressure transducer 112 positioned along a tissue engaging surface 12b of the distal tip 12, as shown in FIG. 2B. Similar to embodiments discussed previously, the tissue supporting member may be inserted through a defect, for example within an annulus fibrosis of the intervertebral disc, such that the tissue engaging surface of the tissue supporting member is positioned distal to tissue on one side of the defect. The tissue supporting member is then pulled proximally, exerting a force $F_R$ against the tissue. The value of pressure obtained from the pressure transducer in response to the force $F_R$ exerted, may be used to determine the stiffness of the tissue. In a specific example, the obtained pressure value may be used to determine the correlating value of tissue stiffness from a range of predetermined values provided in a lookup table.

Tissue Supporting Member Having Surface Modifications

Figure 5:
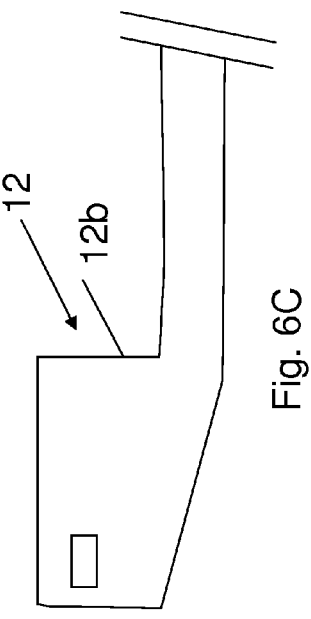
FIG. 5 shows a side view of a tissue supporting member in accordance with an embodiment of the present invention.

In some embodiments, the tissue supporting member such as distal tip 12 of device 100 comprises a rigid or a semi-rigid material. In some embodiments, the tissue supporting member has a rigidity that is substantially greater than the tissue 200 that is being pierced. In some examples, the tissue supporting member comprises a biocompatible material for use in medical device applications, such as metal, metal alloys, or polymers. In one specific example, the tissue supporting member comprises stainless steel, such as "Stainless Steel 304". In one example, the distal tip 12 comprises surface modifications in order to enhance surface area and/or friction between the tissue and the tissue engaging surface 12b of the distal tip 12. Pressure exerted on the tissue by the tissue engaging surface 12b may be reduced by providing a larger surface area with the same (i.e. equal) friction. This may enhance the ability of the distal tip 12 to grip the tissue. In some embodiments, the device distal tip has a rough tissue engaging surface 12b such as a surface having ribs, grooves, cleats, indentations or projections as shown in FIG. 5, to help provide friction between the surface 12b and the tissue and to enhance the tissue engaging ability of surface 12b. In other embodiments, the tissue engaging surface 12b of the distal tip 12 comprises barbs, or hooks to engage the tissue 200. In still other embodiments, the distal tip 12 may use other means to engage the tissue such as vacuum or suction. In some embodiments, the device surface can be modified. For example, surfaces such as that of the device distal tip 12, needle 116, and needle/shuttle assembly 216 can be coated. In one example, coating is applied to enhance ease of entry of the device 100 through tissue, for example, through a defect 300 within the tissue 200. The coating can be a polymer coating such as Teflon. In another example, the supporting surface of the tissue supporting member, such as the tissue engaging/contacting surface 12b of distal tip 12 is coated with a bioadhesive. This allows surface 12b to adhere to the tissue 200 to prevent the tissue 200 from being displaced during puncture.

Tissue Supporting Member Having Alternative Surface Geometries

Figure 6A:
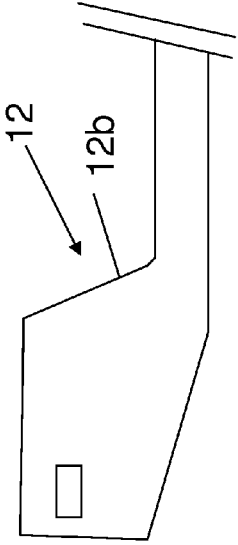
FIGS. 6A-6D show side views of a tissue supporting member in accordance with various embodiments of the present invention.
Figure 6B:
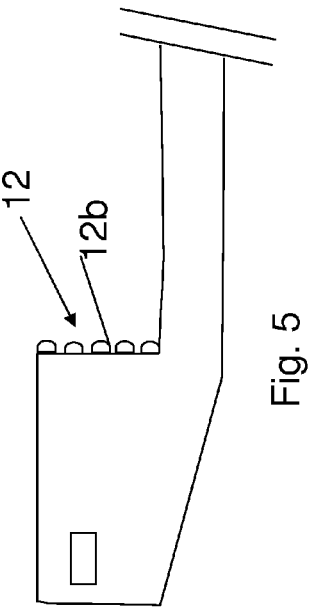
Figure 6C:
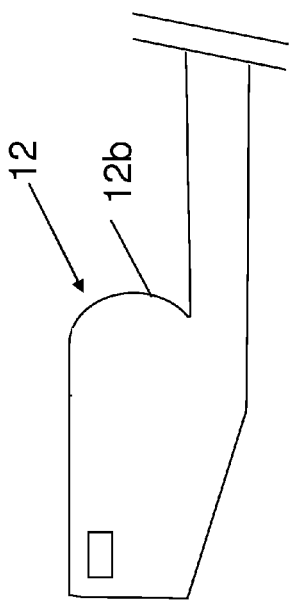
Figure 6D:
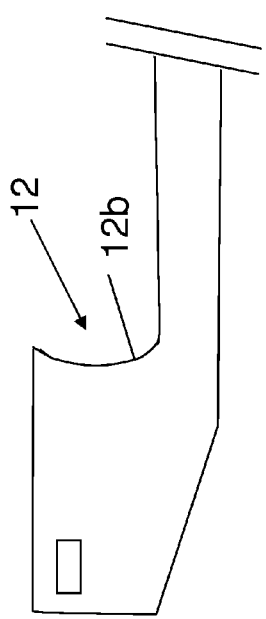

In some embodiments, the tissue engaging surface 12b is substantially convex as shown in FIG. 6A or substantially concave as shown in FIG. 6B. In some embodiments, the tissue engaging surface 12b of distal tip 12 is shaped substantially to conform to the tissue that it is positioned against or engages. In one example, the distal tip 12 is positioned against the inner annulus surface 400 of the intervertebral disc. In a specific example of this, the tissue engaging surface 12b is substantially convex (FIG. 5A) and conforms to the curvature of the inner annulus wall. In some embodiments, the distal tip 12 of device 100 has a substantially flat tissue engaging surface 12b as shown in FIG. 6C. In some embodiments, the tissue supporting member has a tissue engaging surface that is oriented substantially perpendicular to the device longitudinal axis as illustrated in FIG. 6C., the tissue engaging surface 12b is inclined with respect to the device longitudinal axis as shown in FIG. 6D. In other embodiments, the tissue engaging surface 12b may have other configurations. Alternatively, the tissue engaging surface 12b may have a shape that is a combination of the shapes discussed above.

In some embodiments, the device distal end including distal tip 12 has chamfered or rounded corners providing a substantially atraumatic surface. In other embodiments, at least a portion of the device 100, such as the device distal end, has a coating such as a polymer coating to improve atraumaticity. In some examples, anti-inflammatory, anti-bacterial or anti-viral coatings may be applied to a portion of the device 100 to prevent disease, for example when the device is used within the intervertebral disc they may be used to prevent discitis.

Figure 7B:
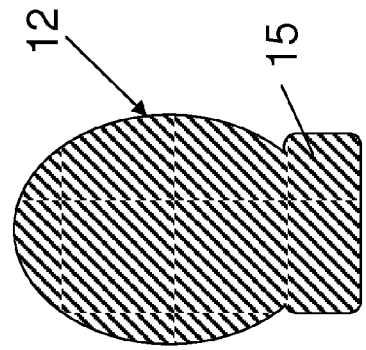
FIGS. 7A-7E show cross-sectional views of a tissue supporting member in accordance with various embodiments of the present invention.
Figure 7C:
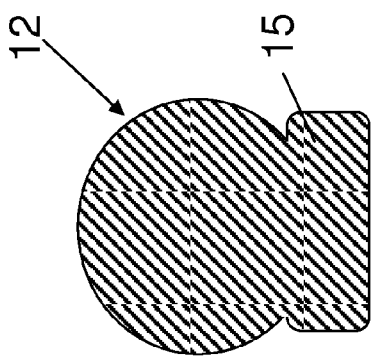
Figure 7A:
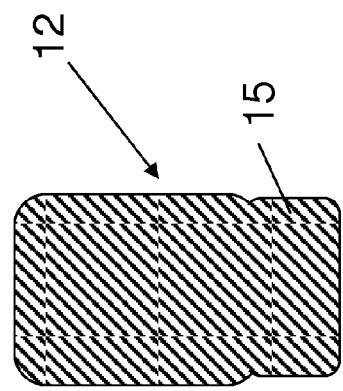

In various embodiments of the device of the present invention, the distal tip 12 of the device 100 may have varying transverse cross-sections. As shown in FIGS. 7A-7C, the distal tip 12 and/or the tissue contacting surface 12b has a substantially rectangular, circular or oval cross-section, respectively. In other embodiments, the distal tip 12 may have any other cross-sectional shapes. In alternate embodiments as shown in FIGS. 7D-7E, the tissue supporting member such as the distal tip 12, and thus the tissue contacting surface 12b, is in the form or configuration of a frame.

Figure 7E:
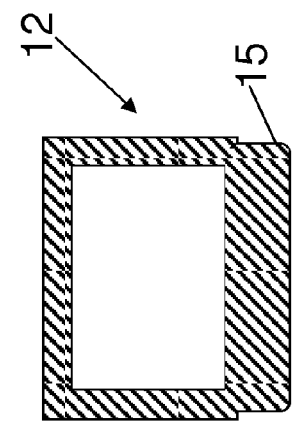
Figure 7D:
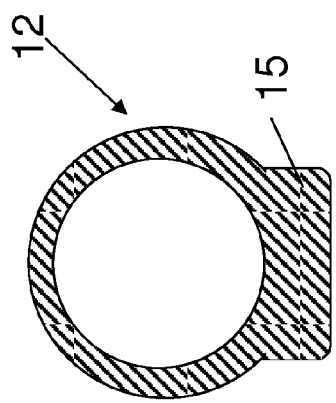

Thus, in some embodiments, the tissue contacting or engaging surface 12b is substantially a continuous solid surface as shown in FIGS. 7A-7C, while in other embodiments the tissue contacting surface 12b is a frame, as shown in FIGS. 7D and 7E with an enclosed hollow interior. As an example, the cross-sectional shape of the frame may be substantially in the form of a circle, oval, square, rectangle, or other polygon. In other examples, the frame may not define a closed interior and, for example, may be open on one side.

Tissue Supporting Member Comprising a Hook

Figure 8B:
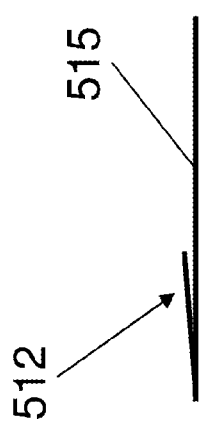
FIGS. 8A-8D show alternative embodiments of a tissue supporting member in accordance with the present invention.
Figure 8C:
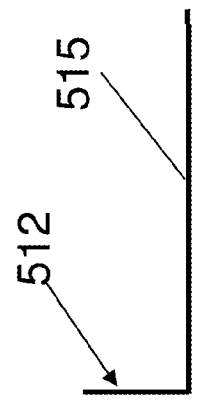
Figure 8D:
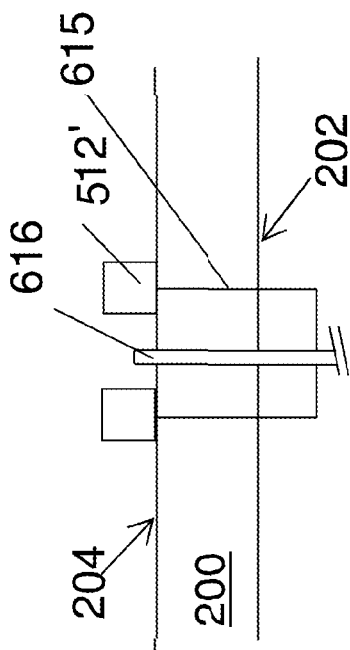
Figure 8A:
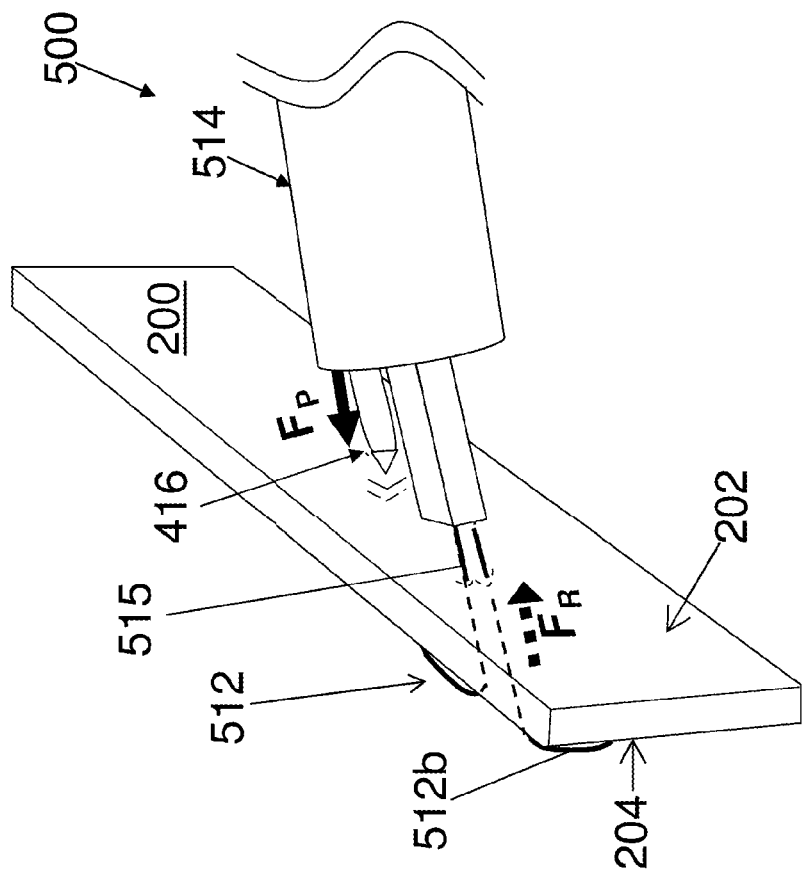

With reference now to FIGS. 8A-8C, and in accordance with an alternate embodiment of the present invention, a device 500 is used to puncture tissue 200. The device 500 is advanced towards one side of the tissue, such as the proximal surface 202 of the tissue 200. The device 500 comprises a tissue supporting member such as, for example, one or more hooks 512. A hook 512 is deployed through tissue 200 such that it transects the tissue 200 and is deployed on the far side, for example the distal side of the tissue 200. A tissue contacting surface 512b of the hook 512 is positioned against the distal surface 204 of the tissue. The hook 512 supports the distal surface 204 of the tissue and allows a tissue puncturing member such as a needle 516 to more readily puncture the tissue 200 at a desired target location by minimizing displacement of the tissue 200 as described hereinabove. The hook 512 and the needle 516 may be integral, i.e. they may be a part of the same device, or they may comprise separate devices. In one example, both the hook 512 and the needle 516 are housed within a proximal region 514 of the device 500 and are deployed as needed. The hook 512 prevents, limits or minimizes tenting of the tissue when the needle 516 is advanced against the tissue 200 by providing a counter or resistive force $F_R$ which opposes the puncturing force $F_P$ exerted by the needle 516, as described hereinabove.

In one specific example, the hook 512 is deployed at the site of a defect within a region of tissue within a patient's body and the device 500 may be used to puncture tissue in the vicinity of a defect. In one specific example, the hook 512 is deployed through defective tissue adjacent a desired puncture site. In another example, the hook 512 is deployed through healthy tissue adjacent the defective tissue, adjacent the desired puncture site. The defect non-limitingly may be a defective, diseased or damaged portion of tissue such as a rip, tear, fissure, hole, herniation, thinning of tissue, degradation of tissue, or a thickened region of tissue.

In one specific example, the hook 512 is shapeable, hinged or otherwise configured to be moveable from a first closed/ folded position, as shown in FIG. 8B (where the hook 512 is substantially folded over the longitudinally extending body or neck 515) to a second deployed position as shown in FIGS. 8A and 8C (where the hook 512 is substantially perpendicular or oblique to the longitudinally extending body or neck 515). The hook 512 in the folded position may ease entry of hook 512 through tissue and may help minimize damage to the tissue as the hook 512 travels through the tissue to the side of the tissue where it is deployed. Once the hook 512 is deployed it supports the tissue 200 thereby allowing the needle 516 to more readily create a puncture through the tissue. Additionally, a mechanism may be provided whereby hook 512 is moved back to its first closed/folded position, so that it may be retracted and removed from the tissue. In some cases, more than one hook 512 is used. In some examples, the hook 512 is, for example, substantially flat, c-shaped or has a shape that substantially conforms to the shape of the tissue.

Alternatively, in some embodiments, as shown in FIG. 8D, the tissue supporting member comprises an anchor 512' attached, for example, to a tether 615 for supporting the tissue prior to puncturing using the tissue puncturing member such as a needle 616. The anchor 512' supports the tissue and may help prevent tenting allowing needle 616 to more readily puncture the tissue. In some embodiments, more than one anchor 512' may be used.

Additional Embodiments

FIGS. 9 to 14 show alternative embodiments of tissue supporting members. Each figure includes anterior-posterior and posterior-anterior isometric views as well as a transverse cross-section and a side A-P view. In some of the figures, the device is not illustrated in all views.

Tissue Supporting Member Comprising an Injectate

Figure 9:
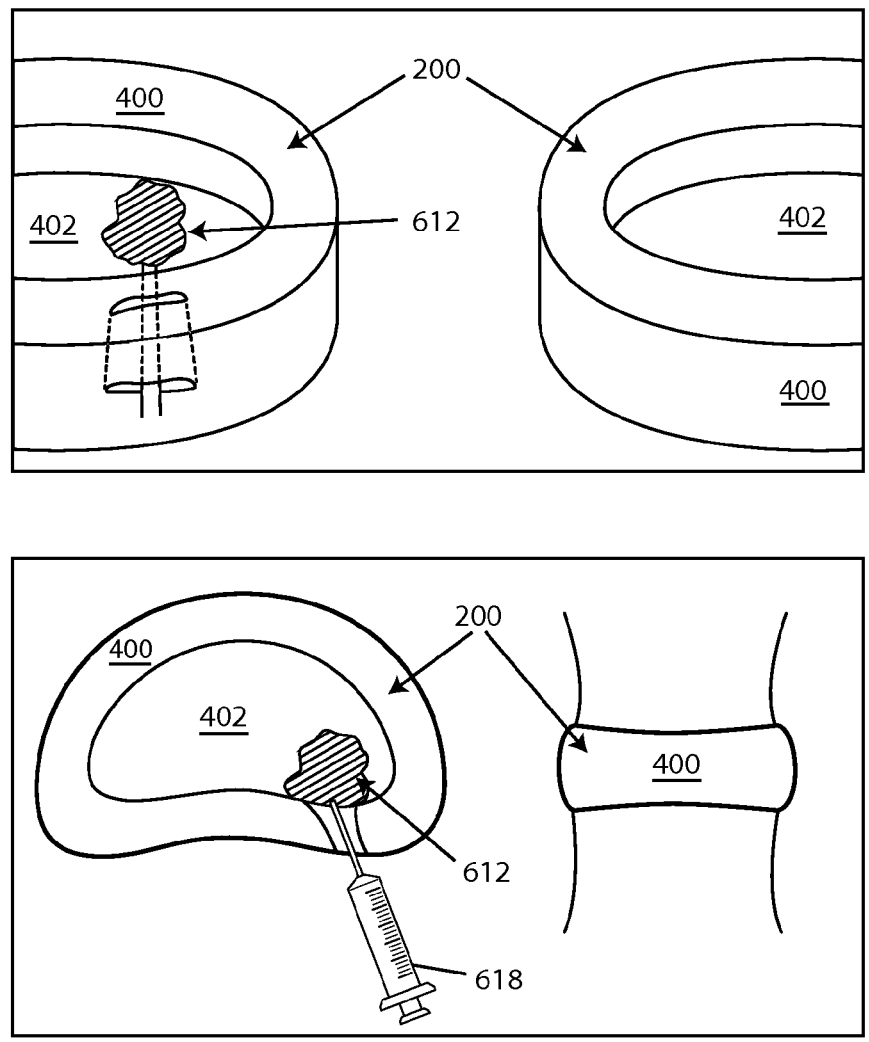
FIG. 9 is an illustration of an alternate embodiment of a tissue supporting member in accordance with a method of the present invention.

In an alternate embodiment of the present invention as shown in FIG. 9, the support may be provided by a tissue supporting member that is an injectate or injected material 612 that is inserted within the interior of the tissue 200. In one embodiment, the material is injected on the inner/interior side of an annulus fibrosis 400 of an intervertebral disc. In other words, the material is injected substantially adjacent the inner surface of the annulus fibrosis 400, such as within the nucleus pulposus 402 of the intervertebral disc. In one example, the material 612 is injected within the intervertebral disc following a nucleotomy or discectomy and fills a void or cavity that has been created within the nucleus pulposus 402. In the illustrated embodiment, the injected material 612 gels in situ (at 37° C.). The material may be, for example, hydrogel, polymer, or bone cement. The hardened gel material provides support for the tissue of the annulus fibrosis. In one example the injected material 612 is degradable. In another example the injected material is non-degradable. After the injected material 612 hardens within the interior of the annulus fibrosis 400, it provides support to more readily allow puncture of the annulus fibrosis. In an example, the injectate 612 is injected using a syringe 618 which may be of any gauge size suitable for injecting into the intervertebral disc. In one specific example, the injectate 612 is injected through a defect within an annulus fibrosis 400 and provides support for puncture of the annulus fibrosis 400. This in some cases assists in repair of the defect, for example, by allowing a suture to be passed between the exterior of the annulus fibrosis to the interior of the annulus fibrosis. In other embodiments, the defect may be repaired using any other technique known in the art.

Tissue Supporting Member Comprising a Balloon

In an alternate embodiment of the present invention as shown in FIG. 10, the support may be provided by a tissue supporting member that is an inflatable member such as an inflatable balloon 712 that is inserted within the interior of the tissue 200. In one embodiment, the inflatable balloon 712 is provided on the inner/interior side of an annulus fibrosis 400 of an intervertebral disc. In other words, the balloon 712 is positioned substantially adjacent the inner surface of the annulus fibrosis 400, such as within the nucleus pulposus 402 of the intervertebral disc. In one embodiment, the balloon is positioned within the nucleus pulposus 402 after a nucleotomy or discectomy procedure. This procedure may create a void or cavity within the nucleus pulposus 402 which may reduce or eliminate support for the tissue of the annulus 400 at that location. In one such example, the balloon 712 is inserted within this cavity and is inflated to provide support for the annulus fibrosis 400 at that location. The balloon 712 may be inflated by, for example, air or a liquid such as water or saline. The balloon may be inserted through an outer cannula or guide 718. The balloon 712 provides support for the tissue of the annulus fibrosis to allow puncture of the annulus fibrosis 400. In one specific example, the balloon 712 is positioned using a cannula as a guide which is inserted through a defect within an annulus fibrosis 400. The balloon 712 provides support to minimize displacement of the annulus tissue to more readily allow puncture of the annulus fibrosis 400. The inflated balloon 712 will provide sufficient pressure against the annular tissue to act as a support. This in some cases assists in repair of the defect, for example, by allowing a suture to be passed between the exterior of the annulus fibrosis to the interior of the annulus fibrosis. In other embodiments, the defect may be repaired using any other technique known in the art.

Tissue Supporting Member Comprising a Frame

In an alternate embodiment of the present invention, the tissue supporting member comprises a rigid support having a distal tip 12 that is inserted within the interior of the tissue 200. In one example, as shown in FIG. 11 and previously in FIGS. 7D-7E, the distal tip 12 and thus the tissue contacting surface 12b are in the shape of a frame 812. In one embodiment, the frame 812 is positioned at the inner/interior side of an annulus fibrosis 400 of an intervertebral disc. In other words, the frame 812 is positioned substantially adjacent the inner surface of the annulus fibrosis 400, such as within the nucleus pulposus 402 of the intervertebral disc. The frame 812 may comprise a biocompatible material, for example stainless steel, or a polymer such as Acrylonitrile butadiene styrene (ABS), Poly ether ether ketone (PEEK), Polypropylene (PP) or Polyethylene (PE). The frame 812 provides support for minimizing displacement of the tissue of the annulus fibrosis to more readily allow puncture of the annulus fibrosis 400 using a tissue puncturing member. In one specific example, the tissue puncturing member is a needle 116 and is inserted through the frame 812 to allow puncture of the annulus fibrosis 400. In one example, the frame 812 may inserted through a defect within the annulus fibrosis 400 to assist in repairing the defect. The frame 812 provides sufficient support for the tissue of the annulus 400 to allow the needle 116 to puncture the tissue. The defect may be repaired by applying a suture for annular approximation. In other embodiments, the defect may be repaired using any other technique known in the art.

Tissue Supporting Member Comprises a Deployable Armature Frame

In still another embodiment as shown in FIG. 12, the tissue supporting member comprises one or more deployable armature frames 912 that is (are) inserted within the interior of the tissue 200. In other words, the tissue supporting member comprises an armature frame 912 that may be pivotally connected to a longitudinally extending component. The armature frame 912 may be inserted through the tissue in a folded position with the armature frame 912 being aligned with the longitudinally extending component. The armature frame 912 may then be deployed or unfolded such that, in some embodiments, it extends substantially perpendicularly or obliquely to the longitudinally extending component and is positioned at the inner/interior side of the tissue 200. In the specific embodiment shown in FIG. 12, armature frame 912 assumes an inverted "L" shape within the intervertebral disc. In one example, the armature frame 912 is positioned substantially adjacent an inner annulus fibrosis 400 of an intervertebral disc. In other words, the armature frame 912 is positioned substantially adjacent the inner surface of the annulus fibrosis 400, such as within the nucleus pulposus 402 of the intervertebral disc. The armature frame 912 provides support for the tissue of the annulus fibrosis to more readily allow puncture of the annulus fibrosis 400 using a tissue puncturing member such as a needle. Thus, tissue of the annulus 400 may be punctured with minimal displacement of the annulus. In one example, the armature frame 912 may be inserted within the intervertebral disc through a defect in order to assist in repairing the defect. The defect may be repaired by applying a suture for annular approximation. In other embodiments, the defect may be repaired using any other technique known in the art. In one embodiment, the armature frame 912 may additionally be coupled to an adjustable component 918 that can slide up and down along the longitudinally extending component or shaft so that it can abut against the annulus fibrosis and compress/clamp the annulus tissue in place with the deployable armature 912 to facilitate puncture.

Tissue Supporting Member Comprises Magnetic Components

Figure 13:
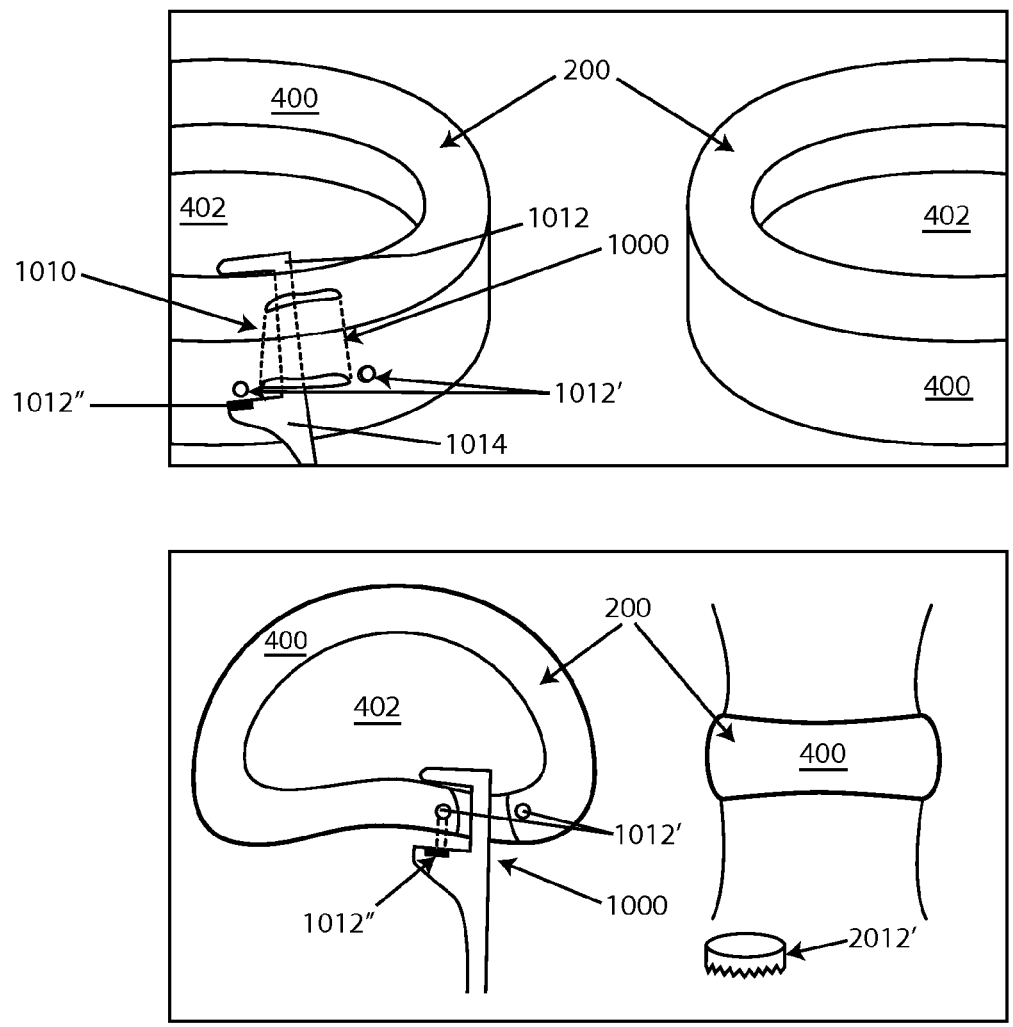
FIG. 13 is an illustration of an alternate embodiment of a tissue supporting member in accordance with a method of the present invention.

In still another embodiment, as shown in FIG. 13, the tissue to be punctured may be supported using a combination of magnets. In one example, a device 1000 comprises a distal end having a tissue supporting member including a distal tip. Device 1000 further comprises a proximal portion 1014 a tissue receiving gap 1010 for receiving tissue located between the proximal portion 1014 and the distal tip 1012. One or more first magnetic components 1012' are adhesively, mechanically or otherwise attached to the tissue near the puncture site. For example, the first magnetic component 1012' is a magnetic cleat 2012' that may be temporarily clamped or implanted within the tissue or otherwise attached to the tissue. The device may be inserted within a patient's body such that tissue is received within the tissue receiving gap. A second magnetic component 1012" is coupled to the device 1000. In one specific example, the second magnetic component 1012" may be embedded within the device 1000. In some embodiments, the second magnetic component 1012" is coupled at or near a distal part of the device proximal portion 1014. In other embodiments, the second magnetic component 1012" is coupled to the device distal end. In a specific example of this, the second magnetic component 1012" is coupled to the distal tip 1012 of the device 1000. The magnetic force between the magnetic components 1012' and 1012" aids to support or hold the tissue as a tissue puncturing member is advanced into the tissue in order to puncture the tissue without displacement of the annulus. In the illustrated example, the device distal tip is positioned on the inner/interior side of an annulus fibrosis 400 of an intervertebral disc. In other words, the device distal tip is positioned substantially adjacent the inner surface of the annulus fibrosis 400, such as within the nucleus pulposus 402 of the intervertebral disc to provide further tissue support. The device distal tip and the magnetic components 1012' and 1012" provide support for the tissue of the annulus fibrosis to allow puncture of the annulus fibrosis 400 using a tissue puncturing member such as a needle. In one example, the device 1000 may be inserted within the intervertebral disc through a defect in order to assist in repairing the defect. The defect may be repaired by applying a suture for annular approximation. In other embodiments, the defect may be repaired using any other technique known in the art.

Methods of Facilitating Tissue Puncturing by Tissue Compression

Figure 14:
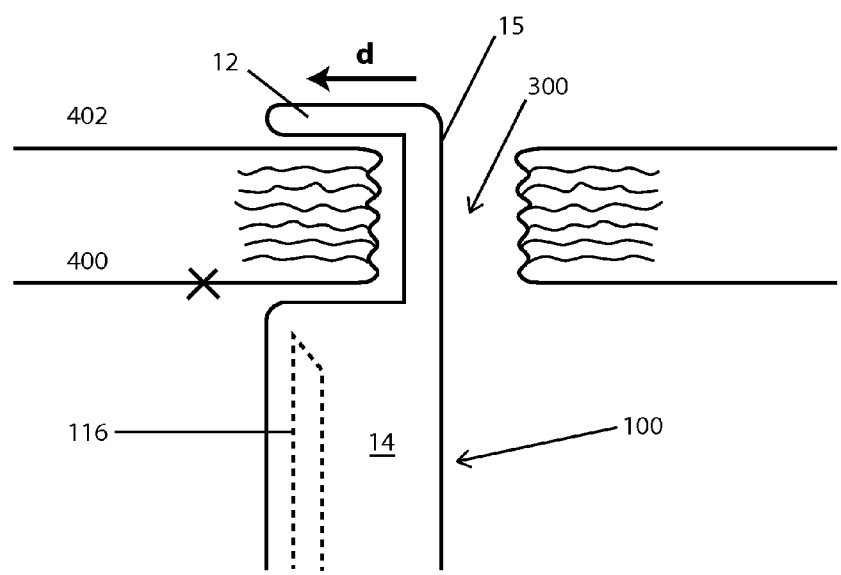
FIG. 14 illustrates a method in accordance with an alternate embodiment of the present invention.

In one broad aspect of the present invention, a method is provided for compressing a region of tissue to facilitate puncturing of the region of tissue. FIG. 14 illustrates a device 100 for implementing the method. In some embodiments, device 100 may be of the type discussed herein above with reference to FIGS. 2A and 2B. As described hereinabove, device 100 comprises a proximal portion 14 and a tissue supporting member that is longitudinally spaced apart from the proximal portion 14, defining a tissue-receiving gap 10. In one embodiment, the tissue supporting member comprises a distal tip 12 that is coupled to the proximal portion 14 via a longitudinally extending neck portion 15. A tissue puncturing member, for example a needle 116 may be housed within the device proximal portion. The device may be inserted into the region of tissue or into a defect within the region of tissue to compress the tissue prior to puncturing.

In one particular example, as shown in FIG. 14, the device 100 is inserted into a defect 300 within an intervertebral disc. The defect 300 may be within the layers of the annulus fibrosis 400 of the intervertebral disc (or within a combination of the annulus fibrosis 400 and the nucleus pulposus 402). The device 100 is inserted through the defect 300, such that a portion of the annulus fibrosis tissue is positioned within the tissue receiving gap 10. The device 100 may be used to create a puncture at a desired target location or site "X" defined within the annulus fibrosis. In one specific example, as the device 100 is inserted within the defect 300, the desired target location or site X for the puncture may not be positioned within the tissue receiving gap, and may be positioned laterally relative to the tissue receiving gap 10.

In one such embodiment, the tissue of annulus fibrosis positioned within the tissue receiving gap 10 may not be of a sufficient stiffness or quality that would allow a fixation device such as a suture that is passed therethrough to be used to approximate the defect. In other words, the tissue may be weak or frayed and may not have sufficient stiffness to withstand the force of approximation $F_a$ (not illustrated) exerted by the suture and thus the suture may pull through the tissue. In still other words, the tissue of the annulus fibrosis within the tissue receiving gap may not be amenable to re-approximation.

Once the device 100 has been inserted into the defect, the longitudinally extending neck portion 15 of the device 100 is used to laterally compress the tissue by translating the device laterally as shown by directional arrow "d" in FIG. 14. The neck portion 15 compresses the tissue to allow a tissue puncturing member to puncture the tissue at the desired target location. Furthermore, the neck portion 15 compresses the annulus fibrosis tissue so that it is sufficiently stiff to allow a tissue puncturing member to puncture the tissue.

Figures 15A, 15B:
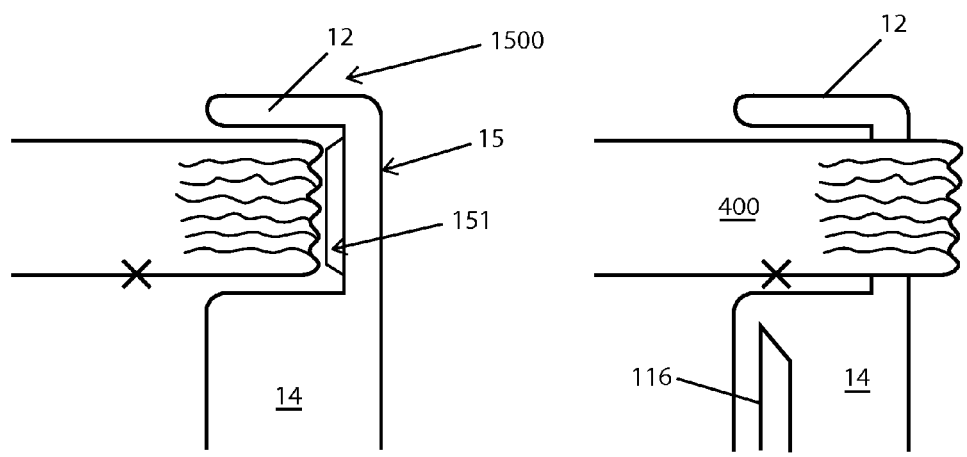
FIGS. 15A-15B illustrate an alternate embodiment of a device for implementing a method of the present invention.

FIG. 15 illustrates an alternative embodiment of a method of the present invention. A device 1500 is disclosed for facilitating puncturing of tissue, wherein the device is similar to embodiments described herein above in FIG. 14. In the device 1500, as shown in FIGS. 15A and 15B, the neck portion 15 further comprises a tissue cutting element 115 such as an electro-cautery knife, a radiofrequency knife or a cutting blade or saw. In some embodiments, the device 100 may be inserted through a defect 300 and the defect defines an edge region of tissue surrounding the defect. In such an embodiment, there may be a substantial amount of frayed or damaged tissue at the boundary or edge region of the defect 300. Thus, even when a device 100 (such as described in FIG. 14) is used to laterally compress the tissue adjacent the defect, the volume of the frayed or damaged tissue may prevent the tissue at the desired target tissue site X from being positioned within the tissue receiving gap 10. In other words the desired tissue site X may be positioned at a distance from the device, such that lateral compression of tissue may not be sufficient to allow the target tissue location X to be positioned within the tissue receiving gap. Alternatively, the amount of frayed, damaged or weak tissue at the boundary of the defect 300 may be unknown. The device 1500 provides a means of passing or sliding the neck portion 15 of the device 1500 laterally through the frayed tissue to allow target tissue location x to be positioned within the tissue receiving gap 10. In some embodiments, the device 1500 may additionally be used to remove or reduce the amount of damaged or frayed tissue at the boundary of the defect by using a tissue cutting element 115 as shown in FIG. 15B. This may allow tissue at the desired target location X, that has sufficient stiffness to be punctured, to be positioned within the tissue receiving gap 10. In one example, where the device 1500 slides laterally through the frayed or damaged portion of the edge region of tissue surrounding the defect, the tissue cutting element 115 may be sharp enough to allow the neck portion 15 of the device to slide through the tissue, or to separate the damaged tissue to allow the device to pass through it while not sliding through a comparatively healthier portion of the annulus tissue at the edge region. The neck portion 15 may then additionally be used to compress the healthier annulus tissue at the edge region so that it is sufficiently stiff to facilitate puncturing. This may allow the device 1500 to pass a tissue puncturing member such as needle 116 through tissue that is amenable to tissue approximation at the desired target location X.

Figure 16:
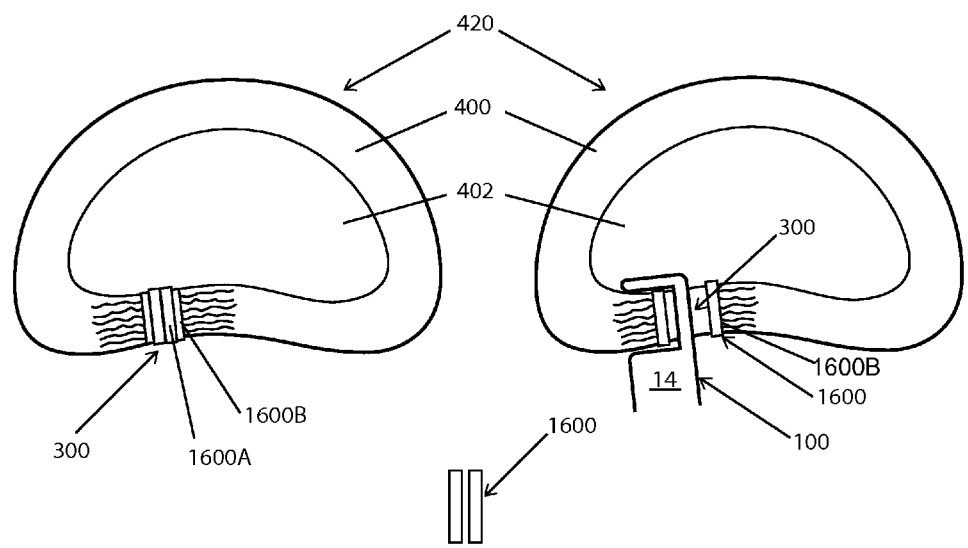
FIG. 16 illustrates another alternate embodiment of a device for implementing a method of the present invention.

In an alternate embodiment as shown in FIG. 16, an alternative means is provided for compression of tissue to facilitate tissue puncturing at the desired target location. A device 1600 is disclosed for radially compressing tissue. In one specific example, the device 1600 comprises a ring positionable within a defect 300 within the intervertebral disc. The tissue is compressed so that it is sufficiently stiff to support or allow a tissue puncturing member to puncture there-through. The ring forces the tissue apart and the tissue is compressed radially around the defect 300. In some embodiments, the device 1600 comprises a series of short cannulae of increasing inner diameter to dilate the defect 300 radially, the cannulae ranging from a first diameter 1600A to a second diameter 1600B. In another embodiment the device 1600 comprises a radially expandable ring that is expandable from a first diameter 1600A to a second diameter 1600B to compress the tissue, such as tissue of the annulus fibrosis 400 of the intervertebral disc 420. In one example, cannulae may be delivered through the defect 300 through a discectomy portal. A device 100 may be inserted into the defect 300 thereafter and used to pass a tissue puncturing member such as a needle to puncture through the compressed tissue that is of sufficient stiffness. Additionally, the needle may be used to pass a fixation device such a suture through the compressed tissue to allow the defect 300 to be approximated.

Figure 17:
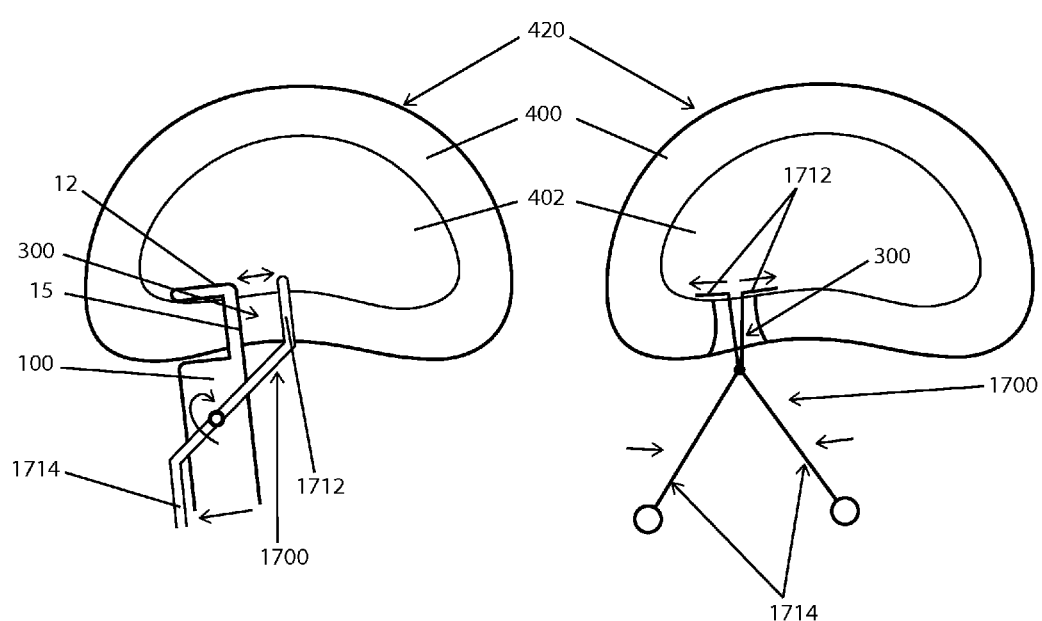
FIG. 17 illustrates still another alternate embodiment of a device for implementing a method of the present invention.
Figure 18:
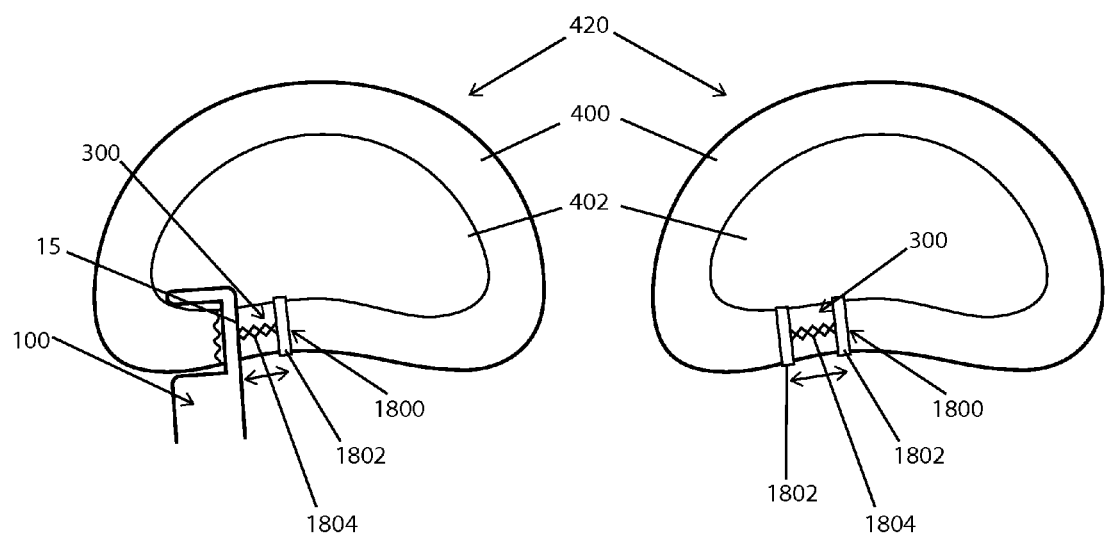
FIG. 18 illustrates an alternative embodiment of a device for implementing a method of the present invention.

In a further alternative of the method of compressing tissue to facilitate puncturing of tissue at the desired target location, a device 1700 is disclosed, as shown in FIG. 17. A device 1700 is provided that may be used to compress the tissue laterally (such as tissue of the annulus fibrosis 400) prior to puncturing the tissue. Device 1700 comprises a device distal portion 1712 and a device proximal portion 1714. Device 1700 is operable to force the tissue open or to pull it apart. In some embodiments, the device 1700 may be coupled to device 100. In one such example, device 1700 is pivotally connected to the device 100, such that pivotal movement of a proximal portion 1714 of the device 1700 towards device 100, forces the distal tip portions 12 and 1712 (of devices 100 and 1700, respectively) apart. This forces the neck region 15 of device 100 laterally against the annulus fibrosis tissue 400, thus laterally compressing the tissue. In another embodiment, device 1700 may be provided separate from the device 100 that is positioned through the defect 300. The device 1700 may comprise two pivotally connected members each having proximal and distal portions 1714 and 1712, respectively. As the proximal portions 1714 of the device 1700 are pushed inwardly, it forces the distal tip portions 1712 apart thus compressing the tissue of the defect laterally. A device 100 may be inserted thereafter to allow tissue 400 to be punctured. In one example, device 1700 is a retractor.

In an alternative embodiment, a device 1800 is disclosed that, similarly to embodiments described previously, may be coupled to device 100 or may operate independently from device 100. In one example, device 1800 comprises a portion 802 that is coupled to device 100 via a spring biased member 804. The spring-biased member 804 is biased towards its expanded position. Device 1800 and device 100 are inserted into the defect when the spring-biased member 804 is in its collapsed position, and it expands thereafter to force device 1800 and device 100 in opposing directions forcing the neck portion 15 of the device 100 to laterally compress the tissue of the annulus fibrosis 400 to facilitate puncturing of the tissue by a tissue puncturing member. In one example, where device 1800 operates independently from device 100, device 1800 is inserted into the defect 300 in its closed position where spring-biased member 1804 is in its collapsed position. It expands thereafter to force the two portions 1802 apart, laterally compressing the tissue of the annulus fibrosis 400. Device 100 may be inserted thereafter to puncture through the compressed tissue.

In accordance with an embodiment of the present invention a method is disclosed for puncturing tissue within a patient's body, such as soft or floppy tissue. An opposing tissue surface which is opposite a desired puncture site is supported, and the tissue is punctured by applying a longitudinally directed force at the desired puncture site of the tissue surface to be punctured. The opposing surface is one of an internal tissue surface and an external tissue surface, and the surface to be punctured is the other one of the internal tissue surface and the external tissue surface.

In one broad aspect, embodiments of the present invention comprise a method of facilitating tissue puncture of a portion of biological tissue using a device, the device comprising a tissue supporting member that is adapted to be placed in a proximal position relative to a portion of the biological tissue and a tissue puncturing member that is adapted to be placed in a distal position relative to the portion of the biological tissue, so that the portion of biological tissue is between the tissue supporting member and tissue puncturing member, the method comprising: supporting the portion of biological tissue using the tissue supporting member; and advancing the tissue puncturing member in a distal direction such that the tissue puncturing member passes through the portion of the biological tissue, thereby puncturing the portion of biological tissue.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, and more particularly in conjunction with specific tissues and/or disease conditions, it is evident that many alternatives, applications, uses, modifications and variations will be apparent to those skilled in the art. Accordingly, it is intended to embrace all such alternatives, applications, uses, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of passing a suture through an intervertebral disc,
    (a) positioning a tissue repair device through a defect in a wall of a tissue of an intervertebral disc;
    (b) pulling said device such that a tissue supporting member of said device abuts a distal surface of the tissue wall and deflects said tissue wall proximally;
    (c) assessing integrity of said tissue wall at or around the deflected tissue;
    (d) selecting a puncturing site at or around said deflected tissue; and
    (e) deploying a puncturing member of said device to puncture said tissue wall at said puncturing site and to deliver a suture through said puncturing site.

2. The method of claim 1, wherein the tissue is selected from the group consisting of an annulus fibrosis of an intervertebral disc, a nucleus pulposus of the intervertebral disc and a combination thereof.

3. A method of facilitating tissue puncture of a tissue wall of a body tissue to pass suture there-through, the method comprising:
    applying an active resistive force against a surface of a wall of a tissue using a tissue supporting member to assess stiffness of the tissue to determine its ability to support a suture under tension; and
    following the step of assessing the stiffness of the tissue, puncturing the tissue wall and passing the suture through the tissue wall, from a substantially unsupported opposite surface opposite said tissue supporting member, using a tissue puncturing member configured for applying a longitudinally directed tissue puncturing force against a region of said opposite surface.

4. The method of claim 3, wherein the tissue comprises spinal tissue.

5. The method of claim 4, wherein the tissue is selected from the group consisting of an annulus fibrosis of an intervertebral disc, a nucleus pulposus of the intervertebral disc and a combination thereof.

6. The method of claim 3, wherein the tissue puncturing member is reciprocally moveable relative to the tissue supporting member for puncturing the tissue wall.

7. The method of claim 3, wherein the steps of applying an active resistive force against a surface of the tissue wall using the tissue supporting member and puncturing the tissue wall using the tissue puncturing member are performed using a single medical device.

8. The method of claim 3, wherein the puncturing force is less than or equal to a biasing force exerted against the tissue wall.

9. The method of claim 3, further comprising the steps of:
    accessing a defect within the tissue prior the step of puncturing the tissue wall; and
    delivering a fixation device through the puncture for repairing the defect.

10. The method of claim 9, wherein the fixation device comprises a tissue anchor.

11. The method of claim 9, wherein the fixation device comprises the suture.

12. The method of claim 9, using a tissue repair device, the tissue repair device comprising a proximal portion coupled to a distal tip and a tissue receiving gap defined there-between, the distal tip defining the tissue supporting member, and the tissue puncturing member comprising a reciprocally moveable needle held within the proximal portion of the tissue repair device, wherein the step of accessing a defect is performed using the distal tip.

13. The method of claim 12, wherein the steps of puncturing the tissue wall and delivering the fixation device are performed substantially simultaneously.

14. The method of claim 13, wherein the fixation device comprises the suture coupled to the needle and wherein the step of puncturing involves advancing the needle and the suture coupled thereto, through the tissue wall.

15. A method of facilitating puncture in an intervertebral disc for suturing therein, a tissue of the intervertebral disc comprising a surface to be punctured and an opposing surface, the method utilizing a medical device comprising a tissue supporting member and a tissue puncturing member, the method comprising:
    (a) positioning the tissue supporting member adjacent the opposing surface of the tissue;
    (b) applying an active resistive force against the opposing surface using the tissue supporting member;
    (c) assessing a stiffness of the tissue based on the amount of displacement of tissue in response to the application of the active resistive force, to determine whether or not the tissue can be punctured using the tissue puncturing member;
    (d) if required, repeating steps (a)-(c) until a suitable puncture site is located; and
    (e) puncturing the tissue at the suitable puncture site using the tissue puncturing member to pass a suture there-through.

16. The method of claim 15, wherein the step of assessing the stiffness of the tissue is performed using a pressure transducer.

17. A method of facilitating tissue puncture of a portion of biological tissue forming the intervertebral disc using a device to enable suturing there-through for disc repair, the device comprising a tissue supporting member that is adapted to be placed in a distal position relative to a portion of the biological tissue and a tissue puncturing member that is adapted to be placed in a proximal position relative to the portion of the biological tissue, so that the portion of biological tissue is between the tissue supporting member and tissue puncturing member, the method comprising:

proximally pulling the portion of biological tissue using the tissue supporting member to assess an integrity of the tissue for supporting suture under tension during approximation of tissue; and upon determining the tissue to be able to support suture under tension, advancing the tissue puncturing member in a distal direction such that the tissue puncturing member passes through the portion of the biological tissue, thereby puncturing the portion of biological tissue to enable suture to be passed there-through.

* * * * *